United States Patent
Delisa et al.

(10) Patent No.: US 10,961,286 B2
(45) Date of Patent: Mar. 30, 2021

(54) NUCLEIC ACIDS, VECTORS, HOST CELLS, AND METHODS FOR RECOMBINANTLY PRODUCING WATER-SOLUBLE MEMBRANE PROTEINS

(71) Applicant: CORNELL UNIVERSITY, Ithaca, NY (US)

(72) Inventors: Matthew Delisa, Ithaca, NY (US); Dario Mizrachi, Ithaca, NY (US)

(73) Assignee: Cornell University, Ithaca, NY (US)

( * ) Notice: Subject to any disclaimer, the term of this patent is extended or adjusted under 35 U.S.C. 154(b) by 545 days.

(21) Appl. No.: 15/504,086

(22) PCT Filed: Aug. 14, 2015

(86) PCT No.: PCT/US2015/045182
§ 371 (c)(1),
(2) Date: Feb. 15, 2017

(87) PCT Pub. No.: WO2016/025781
PCT Pub. Date: Feb. 18, 2016

(65) Prior Publication Data
US 2017/0275343 A1   Sep. 28, 2017

Related U.S. Application Data

(60) Provisional application No. 62/037,760, filed on Aug. 15, 2014.

(51) Int. Cl.
*C07K 14/47* (2006.01)
*C07K 14/705* (2006.01)
*C07K 14/20* (2006.01)

(52) U.S. Cl.
CPC .............. *C07K 14/47* (2013.01); *C07K 14/20* (2013.01); *C07K 14/705* (2013.01); *C07K 2319/03* (2013.01); *C07K 2319/21* (2013.01); *C07K 2319/32* (2013.01)

(58) Field of Classification Search
CPC ...... C07K 14/47; C07K 14/20; C07K 14/705; C07K 2319/21; C07K 2319/32; C07K 2319/03
See application file for complete search history.

(56) References Cited

U.S. PATENT DOCUMENTS

| | | | |
|---|---|---|---|
| 6,096,865 A | 8/2000 | Michaels | |
| 7,048,949 B2 | 5/2006 | Sligar et al. | |
| 7,083,958 B2 | 8/2006 | Sligar et al. | |
| 7,087,729 B1 | 8/2006 | Prive | |
| 7,662,410 B2 | 2/2010 | Sligar et al. | |
| 7,820,806 B2 | 10/2010 | Ernst et al. | |
| 7,829,684 B2 | 11/2010 | Ernst et al. | |
| 8,754,168 B2 | 6/2014 | Dafforn et al. | |
| 2011/0104781 A1 | 5/2011 | Katzen et al. | |
| 2011/0178029 A1 | 7/2011 | Knudsen et al. | |
| 2012/0214741 A1 | 8/2012 | Shoshan-Barmatz et al. | |
| 2012/0252719 A1 | 10/2012 | Zhang et al. | |

FOREIGN PATENT DOCUMENTS

| | | |
|---|---|---|
| EP | 2213747 A1 | 8/2010 |
| WO | 9201715 A1 | 2/1992 |
| WO | 0238609 A2 | 5/2002 |

OTHER PUBLICATIONS

Sadowski et al., Current Opinion in Structural Biology 19:357-362, 2009.*
Witkowski et al., Biochemistry 38:11643-11650, 1999.*
Tang et al., Phil Trans R Soc B 368:Mar. 18, 2012, 1-10, 2013.*
Seffernick et al., J. Bacteriol. 183(8):2405-2410, 2001.*
The NOVAGEN 1998 catalog.*
Kroliczewski et al., Biochimica et Biophysica Acta 1598:177-184, 2002.*
The New England BioLabs pMAL Protein Fusion and Purification System Instruction Manual, p. 17, 2015.*
Kiefer et al., Biochemical Society Transactions 27(6):908-912, 1999.*
International Search Report and Written Opinion for corresponding Application No. PCT/US2015/045182 (dated Nov. 24, 2015).
Costa et al., "Fusion Tags for Protein Solubility, Purification, and Immunogenicity in *Escherichia coli*: The Novel Fh8 System," Front Microbiol. 5(63):1-20 (2014).
Makabe et al., "Atomic Structures of Peptide Self-Assembly Mimics," Proc. Natl. Acad. Sci. 103(47):17753-17758 (2006).
Biancalana et al., "Minimalist Design of Water-Soluble Cross-Beta Architecture," Proc. Natl. Acad. Sci. 107(8):3469-74 (2010).
Borhani et al., "Crystal Structure of Truncated Human Apolipoprotein A-1 Suggests a Lipid-Bound Conformation," Proc. Natl. Acad. Sci. USA 94:12291-96 (1997).
Ortiz-Soto et al., "Expression of Functional Human Sialytransferases ST3Gal1 and ST6Gal1 in *Escherichia coli*," PLoS One 11(5):e0155410 (2016).

* cited by examiner

Primary Examiner — Delia M Ramirez
(74) Attorney, Agent, or Firm — Troutman Pepper Hamilton Sanders LLP (Rochester)

(57) ABSTRACT

The present invention relates to a nucleic acid construct having a chimeric nucleic acid molecule comprising a first nucleic acid moiety encoding an amphipathic shield domain protein; a second nucleic acid moiety encoding an integral membrane protein; and a third nucleic acid moiety encoding a water soluble expression decoy protein, as well as a chimeric nucleic acid molecule having a first nucleic acid moiety encoding an amphipathic shield domain protein and a second nucleic acid moiety encoding an integral membrane protein. The present invention further relates to an expression vector, a host cell, and a protein encoded by the nucleic acid construct. Also disclosed is a method of recombinantly producing an integral membrane protein in soluble form.

22 Claims, 15 Drawing Sheets
Specification includes a Sequence Listing.

| Substrate | $K_d$ ($\mu$M) | |
|---|---|---|
| | EmrE | OspA-EmrE-ApoAI* |
| EtBr | 5.4 ± 0.47 | 6.64 ± 0.31 |
| MV | 75.24 ± 5.64 | 48.47 ± 0.87 |
| TPP⁺ | ND | 124.10 ± 0.70 |

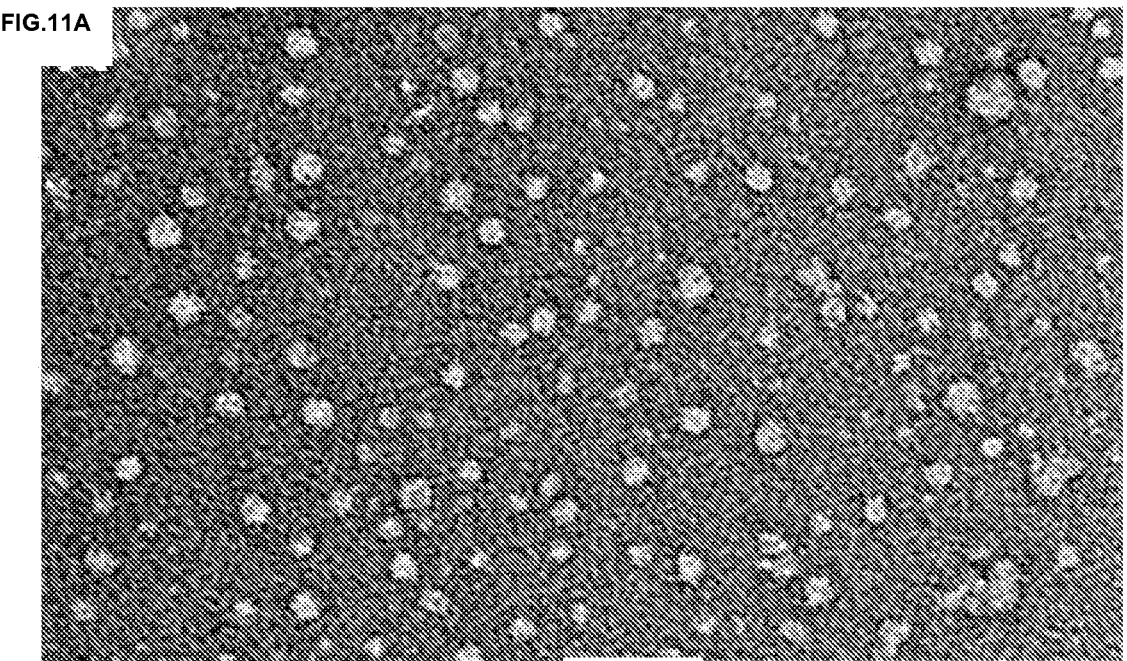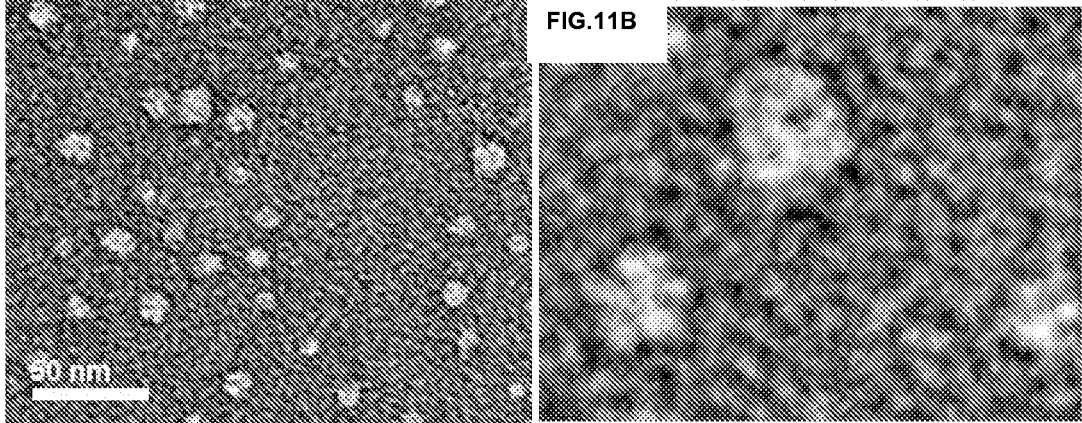

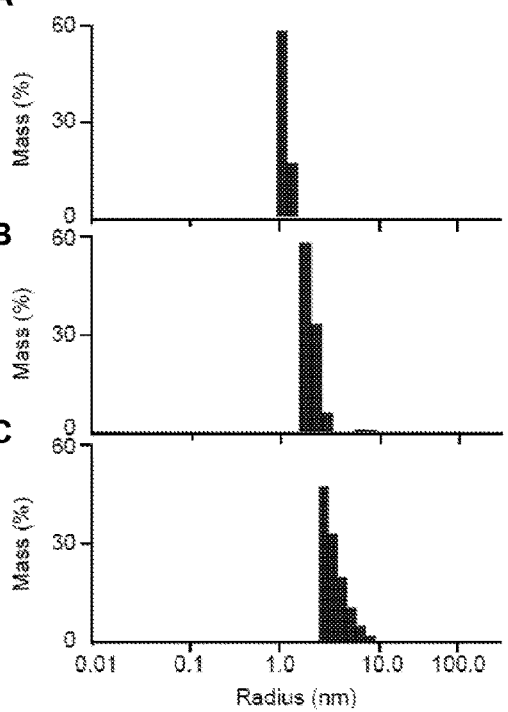
FIG.12A
FIG.12B
FIG.12C
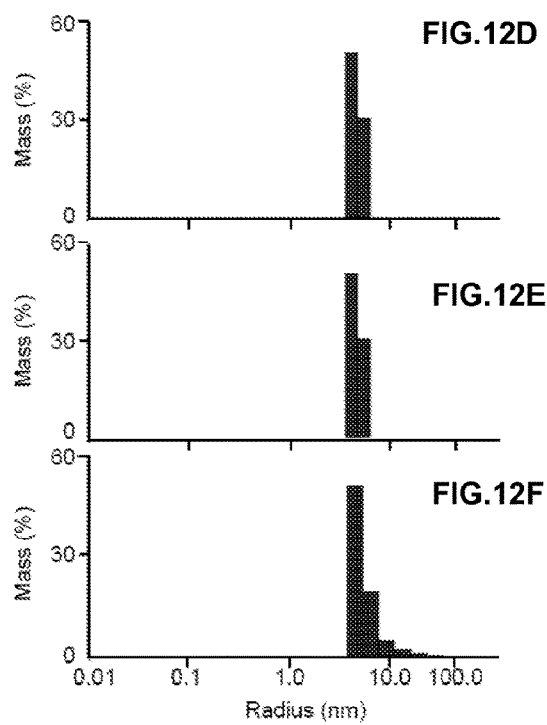
FIG.12D
FIG.12E
FIG.12F

NUCLEIC ACIDS, VECTORS, HOST CELLS, AND METHODS FOR RECOMBINANTLY PRODUCING WATER-SOLUBLE MEMBRANE PROTEINS

This application is a national stage application under 35 U.S.C. § 371 of International Application No. PCT/US2015/045182, filed, Aug. 14, 2015, which claims the benefit of U.S. Provisional Patent Application Ser. No. 62/037,760, filed Aug. 15, 2014, which is hereby incorporated by reference in its entirety.

This invention was made with government support under grant numbers DMR-1332208, DMR-1120296, CBET 1159581, and CBET 1264701 awarded by National Science Foundation and GM-103485, DK089503, R21DA031409-01, and RO1GM086596 awarded by National Institutes of Health. The government has certain rights in the invention.

FIELD OF THE INVENTION

The present invention relates to compositions and methods for making water-soluble integral membrane proteins.

BACKGROUND OF THE INVENTION

Integral membrane proteins (IMPs), which account for nearly one third of all open reading frames in sequenced genomes (Wallin et al., "Genome-Wide analysis of Integral Membrane Proteins from Eubacterial, Archaean, and Eukaryotic Organisms," *Protein Sci.* 7:1029-38 (1998)), play vital roles in all cells including intra- and intercellular communication and molecular transport. Given their centrality in diverse cellular functions, IMPs have enormous significance in disease (Sanders et al., "Disease-Related Misassembly of Membrane Proteins," *Annu. Rev. Biophys. Biomol. Struct.* 33:25-51 (2004); Spiegel et al., "Inherited Diseases Involving G Proteins and G Protein-Coupled Receptors," *Annu. Rev. Med.* 55:27-39 (2004); Spiegelberg et al., "Roles of G-Protein-Coupled Receptor Signaling in Cancer Biology and Gene Transcription," *Curr. Opin. Genet. Dev.* 17:40-44 (2007)) and drug development (Wise et al., "Target Validation of G-Protein Coupled Receptors," *Drug Discov. Today* 7:235-46 (2002); Hopkins et al., "The Druggable Genome," *Nat. Rev. Drug Discov.* 1:727-730 (2002); Rajendran et al., "Subcellular Targeting Strategies for Drug Design and Delivery," *Nat. Rev. Drug Discov.* 9:29-42 (2010)). However, understanding of this important class of proteins is hampered in part by a lack of generally applicable methods for overexpression and purification, two critical steps that typically precede functional and structural analysis.

Most IMPs are naturally of low abundance and must be overproduced using recombinant systems (Wagner et al., "Rationalizing Membrane Protein Overexpression," *Trends Biotechnol.* 24:364-71 (2006); Tate, C. G., "Overexpression of Mammalian Integral Membrane Proteins for Structural Studies," *FEBS Lett.* 504:94-98 (2001)). However, the yields of chemically and conformationally homogenous, active protein following overexpression in bacteria, yeast, insect cells or cell-free systems are often still too low to support functional and/or structural characterization, and can be further confounded by aggregation and precipitation issues. This limitation can sometimes be overcome using protein engineering whereby fusion partners are used to increase expression and promote membrane integration (Roosild et al., "NMR Structure of Mistic, A Membrane-Integrating Protein for Membrane Protein Expression," *Science* 307:1317-21 (2005)). Alternatively, mutations can be introduced to the IMP itself that enhance its stability (Scott et al., "Stabilizing Membrane Proteins Through Protein Engineering," *Curr. Opin. Chem. Biol.* 17:427-35 (2013)) or even render it water soluble (Slovic et al., "Computational Design of Water-Soluble Analogues of the Potassium Channel KcsA," *Proc. Natl. Acad. Sci. U.S.A.* 101:1828-33 (2004)). However, these approaches are largely trial and error, and the identification of suitable fusion partners or stabilizing mutations is neither trivial nor generalizable. Even when appropriate yields can be obtained, the hydrophobic nature of IMPs requires their solubilization in an active form, which is achieved mainly through the use of detergents that strip the protein from its native lipid environment and provide a lipophilic niche inside a detergent micelle. Because IMPs interact uniquely with each detergent, identifying the best detergents often involves lengthy and costly trials. A number of detergent-like amphiphiles have been developed that stabilize IMPs in solution including protein-based nanodiscs (Boldog et al., "Nanodiscs Separate Chemoreceptor Oligomeric States and Reveal Their Signaling Properties," *Proc. Natl. Acad. Sci. U.S.A.* 103:11509-14 (2006)), peptide-based detergents and nanostructures (McGregor et al., "Lipopeptide Detergents Designed for the Structural Study of Membrane Proteins," *Nat. Biotechnol.* 21:171-6 (2003); Schafmeister et al., "Structure at 2.5 A of a Designed Peptide that Maintains Solubility of Membrane Proteins," *Science* 262:734-8 (1993); Zhao et al., "Designer Short Peptide Surfactants Stabilize G Protein-Coupled Receptor Bovine Rhodopsin," *Proc. Natl. Acad. Sci. U.S.A.* 103:17707-12 (2006); Tao et al., "Engineered Nanostructured Beta-Sheet Peptides Protect Membrane Proteins," *Nat. Methods* 10:759-61 (2013)), amphiphilic polymers (Tribet et al., "Amphipols: Polymers That Keep Membrane Proteins Soluble in Aqueous Solutions," *Proc. Natl. Acad. Sci. U.S.A.* 93:15047-50 (1996)), and others (Chae et al., "Maltose-Neopentyl Glycol (MNG) Amphiphiles for Solubilization, Stabilization and Crystallization of Membrane Proteins," *Nat. Methods* 7:1003-8 (2010); Zhang et al., "New Amphiphiles for Membrane Protein Structural Biology," *Methods* 55:318-23 (2011)). While these have helped to increase knowledge of IMPs, each type of amphiphile has its own limitations, and no universal reagent has been developed for wide use with structurally diverse IMPs.

The present invention is directed to overcoming these and other deficiencies in the art.

SUMMARY OF THE INVENTION

A first aspect of the present invention relates to a nucleic acid construct. The construct includes a chimeric nucleic acid molecule comprising a first nucleic acid moiety encoding an amphipathic shield domain protein; a second nucleic acid moiety encoding an integral membrane protein; and a third nucleic acid moiety encoding a water soluble expression decoy protein. The first nucleic acid moiety is coupled to the second nucleic acid moiety's C-terminus and the third nucleic acid moiety is coupled to the second nucleic acid moiety's N-terminus. The coupling may be direct or indirect.

A second aspect of the invention relates to an expression vector including the nucleic acid construct of the present invention.

A third aspect of the present invention relates to a host cell comprising the nucleic acid construct of the present invention.

A fourth aspect of the present invention relates to a chimeric nucleic acid molecule. The molecule includes a first nucleic acid moiety encoding an amphipathic shield domain protein and a second nucleic acid moiety encoding an integral membrane protein. The first nucleic acid moiety is coupled directly or indirectly to the second nucleic acid moiety's C-terminus.

A fifth aspect of the present invention relates to a method of recombinantly producing an integral membrane protein in soluble form. The method includes providing the host cell of the present invention and culturing the host cell under conditions effective to express the integral membrane protein in a water soluble form within the host cell.

A sixth aspect of the present invention relates to a chimeric protein. The chimeric protein includes an amphipathic shield domain protein moiety; an integral membrane protein moiety; and a water soluble expression decoy protein moiety. The amphipathic shield protein moiety is coupled to the integral membrane protein moiety's C-terminal domain and the water soluble expression decoy protein moiety is coupled to the integral membrane protein moiety's N-terminal domain.

Integral membrane proteins (IMPs) play crucial roles in all cells and represent attractive pharmacological targets. However, functional and structural studies of IMPs are hindered by their hydrophobic nature and the fact that they are generally unstable following extraction from their native membrane environment using detergents. Here, a general strategy is devised for in vivo solubilization of IMPs in structurally relevant conformations without the need for detergents or mutations to the IMP itself, as an alternative to extraction and in vitro solubilization. This technique, called SIMPLEx (solubilization of IMPs with high levels of expression), allows direct expression of soluble products in living cells by simply fusing an IMP target with truncated apolipoprotein A-I, which serves as an amphipathic proteic "shield" that sequesters the IMP from water and promotes its solubilization.

Amphipathic proteins display both hydrophilic and hydrophobic surfaces and are often associated with lipids as membrane anchors or involved in their transport as soluble particles. One example is the major component of high-density lipoprotein (HDL) named apolipoprotein A-I (ApoAI), which avidly binds phospholipid molecules and organizes them into soluble bilayer structures or discs that readily accept cholesterol. ApoAI contains a globular N-terminal domain (residues 1-43) and a lipid-binding C-terminal domain (residues 44-243). Biophysical studies suggest that ApoAI exhibits remarkable structural flexibility (Gursky et al., "Thermal Unfolding of Human High-Density Apolipoprotein A-1: Implications for a Lipid-Free Molten Globular State," *Proc. Natl. Acad. Sci. U.S.A.* 93:2991-5 (1996), which is hereby incorporated by reference in its entirety), adopting a molten globular-like state for lipid-free apoA-1 under near-physiological conditions that may allow it to adapt to the significant geometry changes of the lipids with which it interacts. In support of this flexibility, truncation variants of human ApoAI lacking its 43-residue globular N-terminal domain (hereafter ApoAI*) have the ability to form nanodiscs into which detergent-solubilized IMPs can partition (Boldog et al., "Nanodiscs Separate Chemoreceptor Oligomeric States and Reveal Their Signaling Properties," *Proc. Natl. Acad. Sci. U.S.A.* 103:11509-14 (2006), which is hereby incorporated by reference in its entirety). Based on this observation, it is hypothesized that ApoAI* could promote soluble expression of an IMP fusion partner by providing a molecular "shield" that effectively sequesters the large lipophilic surfaces of the IMP from water. To test this hypothesis, chimeras are designed in which ApoAI* is genetically fused to the C-terminus of an IMP target. Expression of these chimeras in the cytoplasm of *Escherichia coli* yields appreciable amounts of globular, water-soluble IMPs that are stabilized in a hydrophobic environment and retain structurally relevant conformations. The SIMPLEx (solubilization of IMPs with high levels of expression) approach provides a facile method for efficiently solubilizing structurally diverse IMPs as a prelude to functional and structural studies, all without the need for detergents or lipid reconstitutions. Using SIMPLEx, a bacterial and human IMP at both the biochemical and biophysical level were able to be studied in detail.

BRIEF DESCRIPTION OF THE DRAWINGS

FIG. 1A shows a Western blot analysis of soluble (sol), detergent solubilized (det), and insoluble (ins) fractions prepared from *E. coli* strain BL21 (DE3) expressing either EmrE, OspA-EmrE, OspA-ApoAI*, or OspA-EmrE-ApoAI* as indicated. The blot was probed with anti-His antibody. Molecular weight (MW) markers are shown on the left. FIG. 1B shows fluorescence microscopy of BL21(DE3) cells expressing the same constructs in FIG. 1A that were each modified with a C-terminal GFP fusion for visualizing protein expression and localization. FIG. 1C shows ligand-binding activity performed using dimeric, detergent-free OspA-EmrE-ApoAI* or organic-extracted detergent-solubilized EmrE, both of which were purified from BL21(DE3) cells. Assays were performed with ethidium bromide (EtBr) as substrate. Determination of binding constants was based on fluorescence quenching. Data is expressed as the mean of biological quadruplicates and the error is defined as the standard error of the mean (SEM) was <5%.

FIG. 2A shows a Western blot analysis of soluble (sol), detergent solubilized (det), and insoluble (ins) fractions prepared from *E. coli* strain BL21 (DE3) expressing either cyt b5, OspA-cyt b5, OspA-ApoAI*, or OspA-cyt b5-ApoAI* as indicated. The blot was probed with anti-His antibody. Molecular weight (MW) markers are shown on the left. FIG. 2B displays size exclusion chromatography (SEC) profiles of $Ni^{2+}$-purified ΔspMBP-cyt b5-ApoAI*. Protein elutes as an octamer (O) or tetramer (T). FIG. 2C shows oxidized and reduced spectra of ΔspMBP-cyt b5-ApoAI* with characteristic peaks at 424 and 409 nm, respectively. FIG. 2D shows coordination of heme cofactor by cyt b5. Cells carrying empty plasmid control or expressing ΔspMBP-cyt b5-ApoAI* were visually inspected for characteristic red heme coloring. Purified ΔspMBP-cyt b5-ApoAI* is also shown. FIG. 2E illustrates augmentation of CYP17A1 lyase activity by cyt b5. CYP17A1 and its substrate 17-hydroxy pregnenolone (17-P5) were incubated with different concentrations (5-25 pmol) of wild-type cyt b5 (detergent solubilized) or ΔspMBP-cyt b5-ApoAI*, or in the absence of cyt b5. The percentage of dehydroepiandrosterone (DHEA) product formed was monitored by HPLC.

(FIG. 3A) ΔspMBP-IMP-ApoAI*; (FIG. 3B) ΔspMBP-IMP; or (FIG. 3C) IMP alone. The IMP targets included (from left to right):

(lanes 1-3) EmrE with OspA decoy (0); (lanes 4-6) EmrE with ΔspMBP decoy; (lanes 7-9) *H. sapiens* cyt $b_5$; (lanes 10-12) *H. sapiens* HSD17B3; (lanes 13-15) *H. sapiens* GluA2; (lanes 16-18) *E. coli* DsbB; (lanes 19-21) *H. sapiens* CLDN1; (lanes 22-24) *H. sapiens* CLDN3; (lanes 25-27) *H. sapiens* S5aR1; (lanes 28-30) *H. sapiens* S5αR2; (lanes 31-33) *Halobacterium* sp. NRC-1 bR; (lanes 34-36) *E. coli* OmpX; and (lanes 37-39) *R. norvegicus* VDAC1. Dashed-line boxes denote the soluble, detergent solubilized, and insoluble fractions prepared for each IMP target. Blots were probed with anti-His antibody. Molecular weight (MW) markers are shown on the left.

Figure 4A:
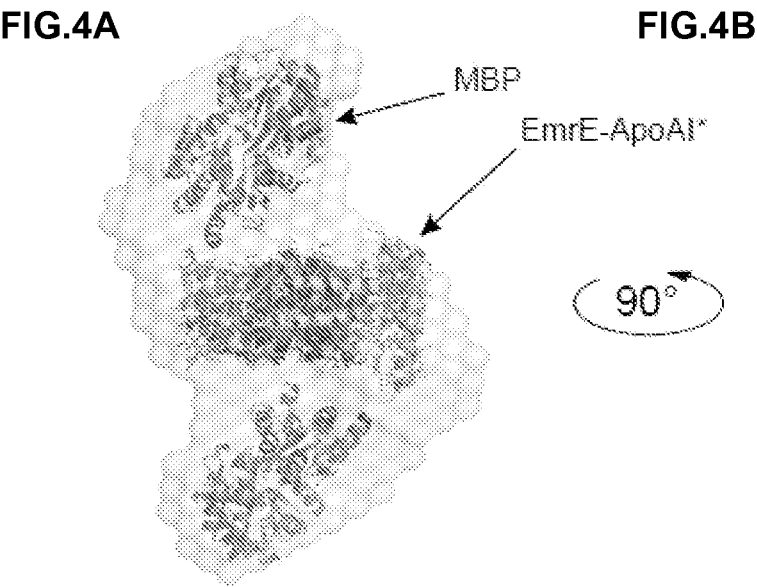
Figure 4B:
Figure 4C:
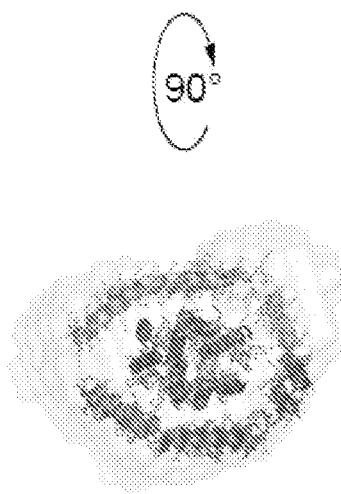
Figure 4D:
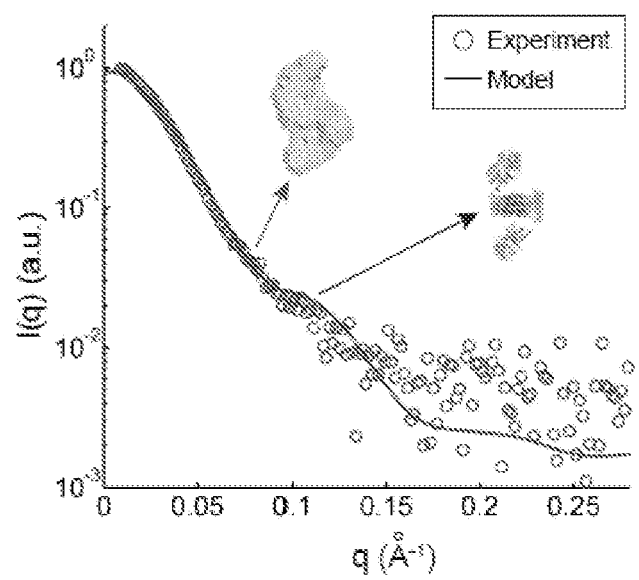

FIGS. 4A-4D show structural characterization of ΔspMBP-EmrE-ApoAI* by SAXS. FIGS. 4A-4C display multiple views of the reconstructed particle envelope calculated ab initio from the dimer SAXS data (circles in FIG. 4D) using DAMMIF (Franke et al., "DAMMIF, a Program for Rapid Ab-Initio Shape Determination in Small-Angle Scattering," *J. Appl. Cryst.* 42:342-6 (2009), which is hereby incorporated by reference in its entirety). The structural model with the lowest chi-square value is docked into the envelope using SUPCOMB. The images represent (FIG. 4A) side view, (FIG. 4B) lateral view, rotated −90° around z-axis from view in (FIG. 4A), and (FIG. 4C) top view, rotated −90° around y-axis from view in (FIG. 4A). ΔspMBP proteins were removed from the representation in c to enhance visualization of the modeled interactions between EmrE and ApoAI*. The model was constructed using ΔspMBP crystal structure (pdb ID: 1NL5), ApoAI lipid free crystal structure (pdb ID: 2A01), and electron microscopy-derived structure of dimeric EmrE (pdb ID: 2168). EOM analysis provided the structural framework for this model. FIG. 4D shows a comparison between the experimental scattering profile of the dimer (circles) and the theoretical profile calculated for the proposed model using CRYSOL (solid line). Goodness of fit is accessed by a chi-square test. A chi-square value of 0.174 indicates that the calculated SAXS curve agrees with the experimental data within error, consistent with the good alignment observed between the proposed model and the reconstruction in FIG. 4A-4C.

Figure 5A:
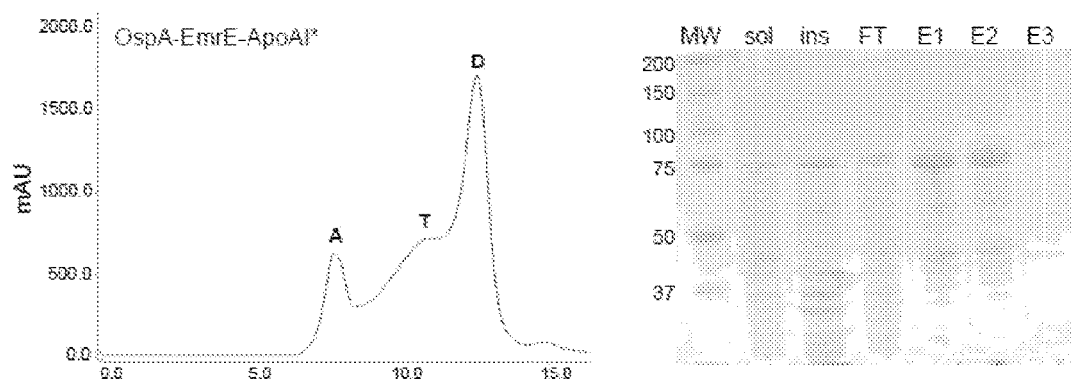
Figure 5B:
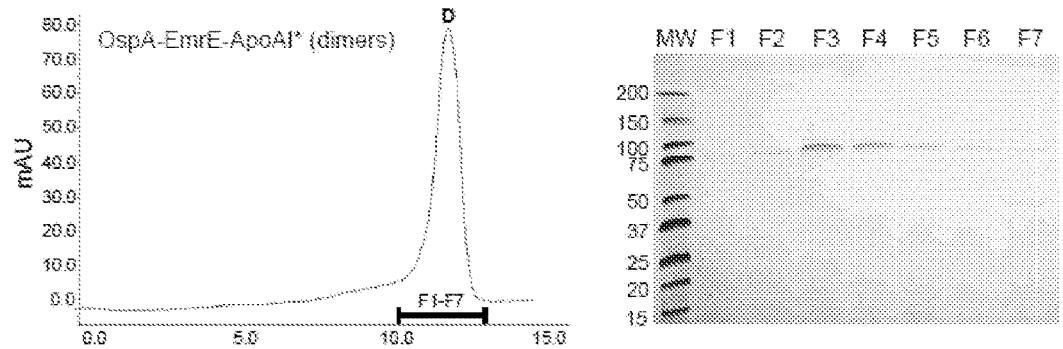
Figure 5C:
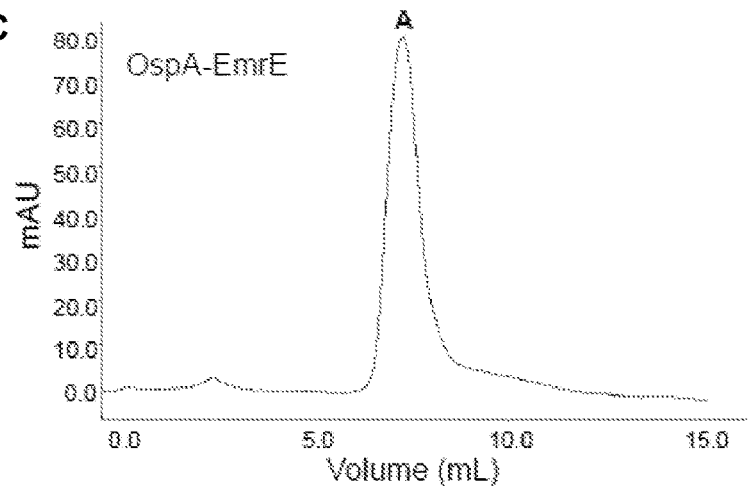

FIGS. 5A-5C illustrate size exclusion chromatography of EmrE constructs. FIG. 5A shows a SEC profile of $Ni^{2+}$-affinity chromatography purified OspA-EmrE-ApoAI* over Superdex 200 10/300 GL (GE Healthcare). The distinguishable species are labeled as aggregates (A), tetramers (T), and dimers (D). The Coomassie-stained gel showing soluble (sol), insoluble (ins) and flow-through (FT) fractions as well as elution fractions (E1-E3) from $Ni^{2+}$-affinity column. Molecular weight (MW) ladder is shown on the left. In FIG. 5B, p Pooled dimer fractions containing dimers of OspA-EmrE-ApoAI* were reapplied to the Superdex 200 column. The profile indicates that dimers in solution remain homogeneous and monodisperse. Bar indicates SEC fractions F1-F7 collected for SDS-PAGE analysis. Coomassie-stained gel showing SEC fractions F1-F7 as indicated. Molecular weight (MW) ladder is shown on the left. FIG. 5C shows a SEC profile of $Ni^{2+}$-affinity chromatography purified OspA-EmrE over Superdex 200 10/300 GL (GE Healthcare). OspAEmrE elutes exclusively as an aggregated protein.

Figure 6A:
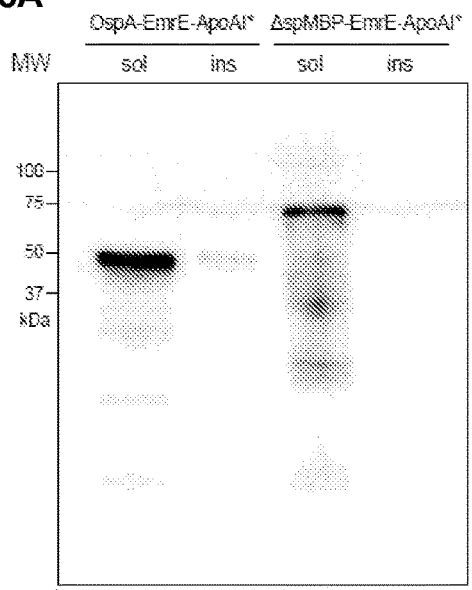
Figure 6B:
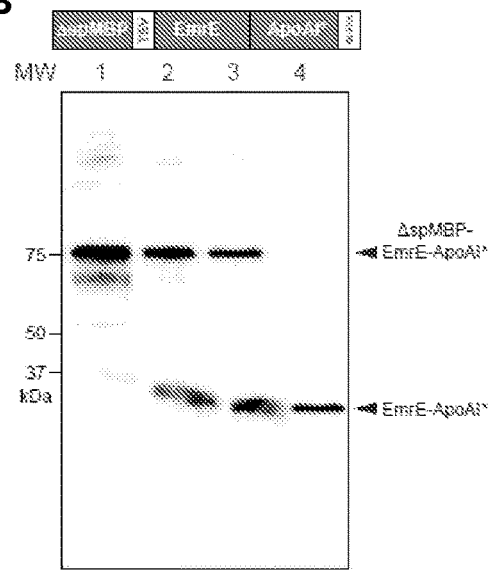
Figure 6C:
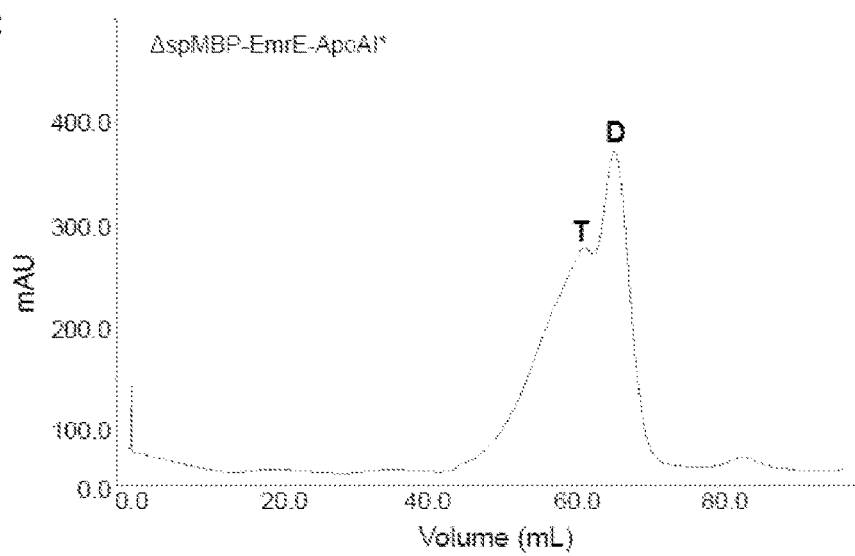

FIGS. 6A-6C show the use of ΔspMBP as an alternative soluble "decoy" protein. FIG. 6A shows a western blot analysis of soluble (sol) and insoluble (ins) fractions prepared from *E. coli* strain BL21(DE3) expressing either OspA-EmrE-ApoAI* or spMBP-EmrE-ApoAI* as indicated. FIG. 6B shows a western blot analysis of purified ΔspMBP-TEV-EmrE-ApoAI* that was (1) untreated, (2) treated with TEV protease in solution, (3) treated with TEV on amylose column, then eluted, and pulled down with $Ni^{2+}$-affinity column; or (4) treated with TEV on amylose column and collected as flow-through. FIG. 6C shows a SEC profile of amylose chromatography-purified spMBP-EmrE-ApoAI* over Superdex 200 pg 16/600 (GE Healthcare). The distinguishable species are labeled as tetramers (T) and dimers (D).

Figure 7A:
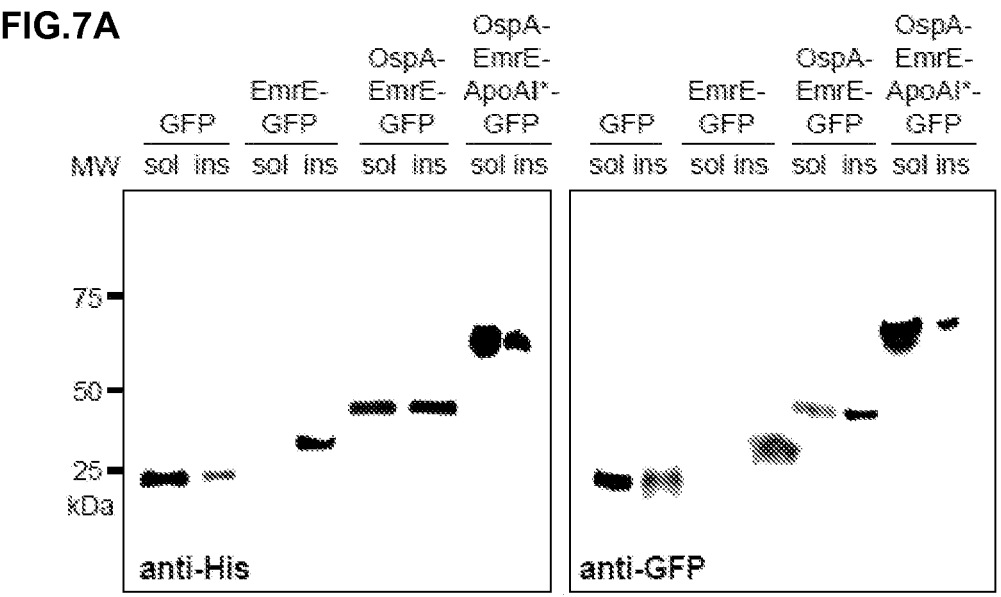
Figure 7B:
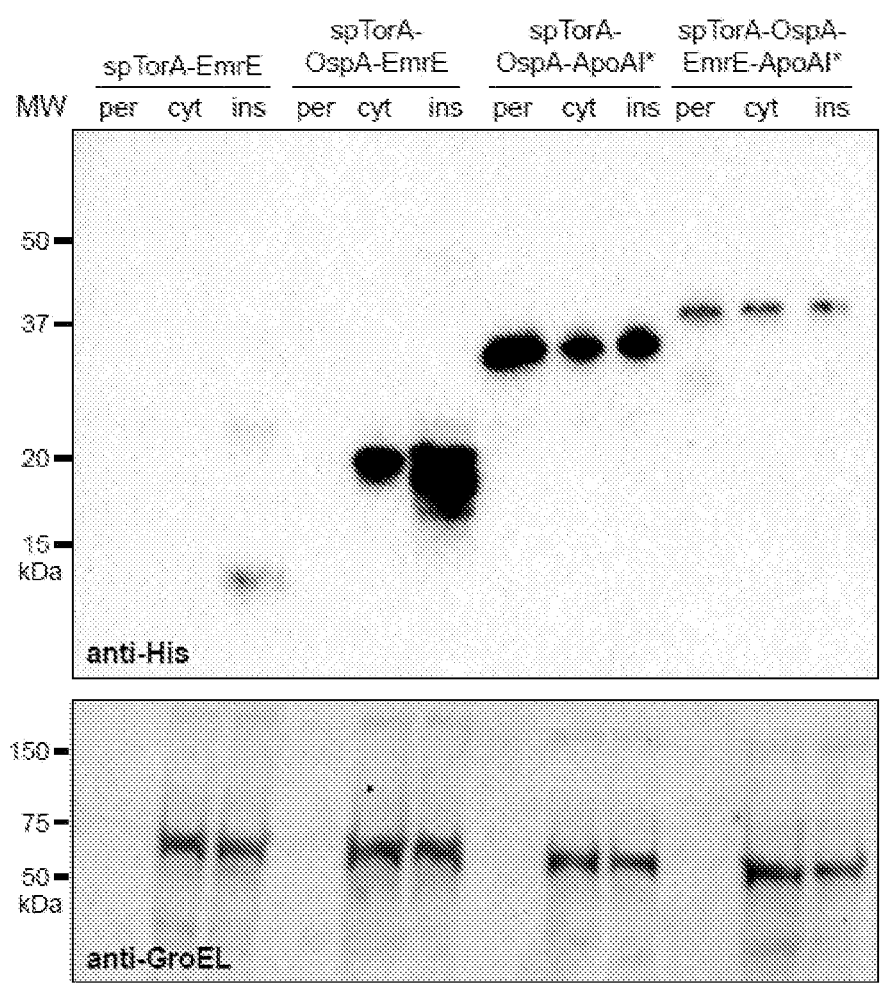

FIGS. 7A-7B show subcellular accumulation of GFP- and spTorA-tagged EmrE. FIG. 7A shows a western blot analysis of soluble (sol) and insoluble (ins) fractions prepared from *E. coli* strain BL21(DE3) expressing GFP-tagged constructs as indicated. Fusions were detected with anti-His (left panel) or anti-GFP (right panel) antibodies. FIG. 7B shows a western blot analysis of periplasmic (per), cytoplasmic (cyt), and insoluble (ins) fractions prepared from *E. coli* strain BL21(DE3) expressing either spTorA-EmrE, spTorAOspA-EmrE, spTorA-OspA-ApoAI*, or spTorA-OspA-EmrE-ApoAI* as indicated. Different fusions were detected with anti-His antibody (top panel) while the quality of fractionations was verified by probing with anti-GroEL antibody (bottom panel). Molecular weight (MW) markers are shown on the left.

Figure 8:
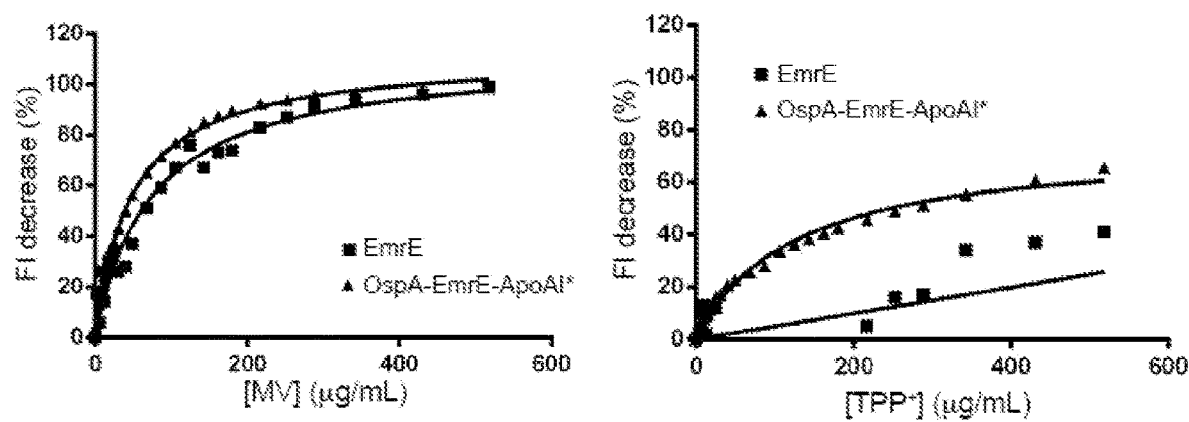

FIG. 8 shows ligand-binding activity of solubilized EmrE. Activity of dimeric, detergent-free OspA-EmrE-ApoAI* or organic-extracted detergent-solubilized EmrE, both of which were purified from BL21(DE3) cells. Activity assays were performed with methyl viologen (MV), or tetraphenylphosphonium (TPP+) as substrates. Data is expressed as the mean of biological triplicates where the standard error of the mean (SEM) was <5%.

Figure 9A:
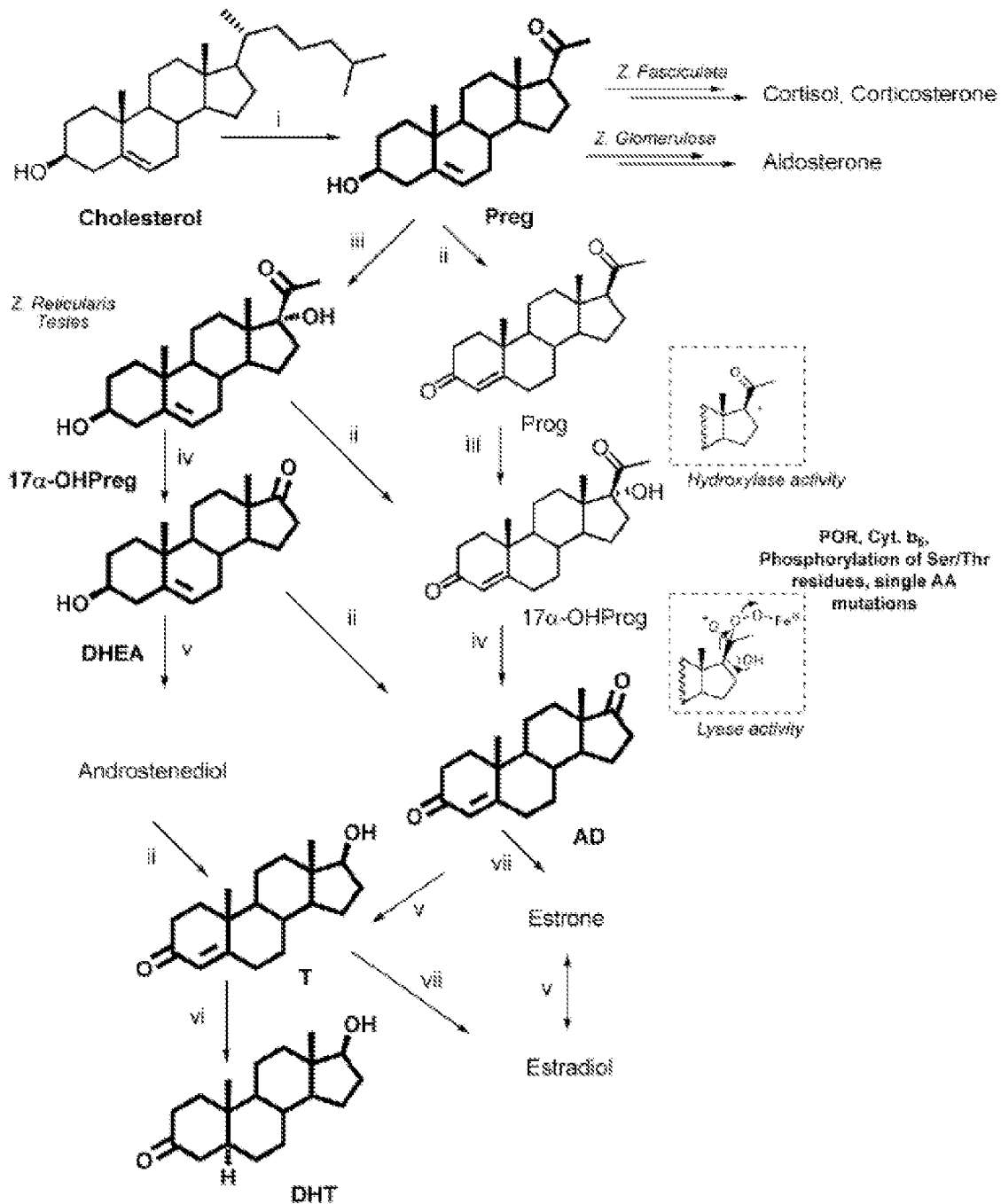
Figure 9B:
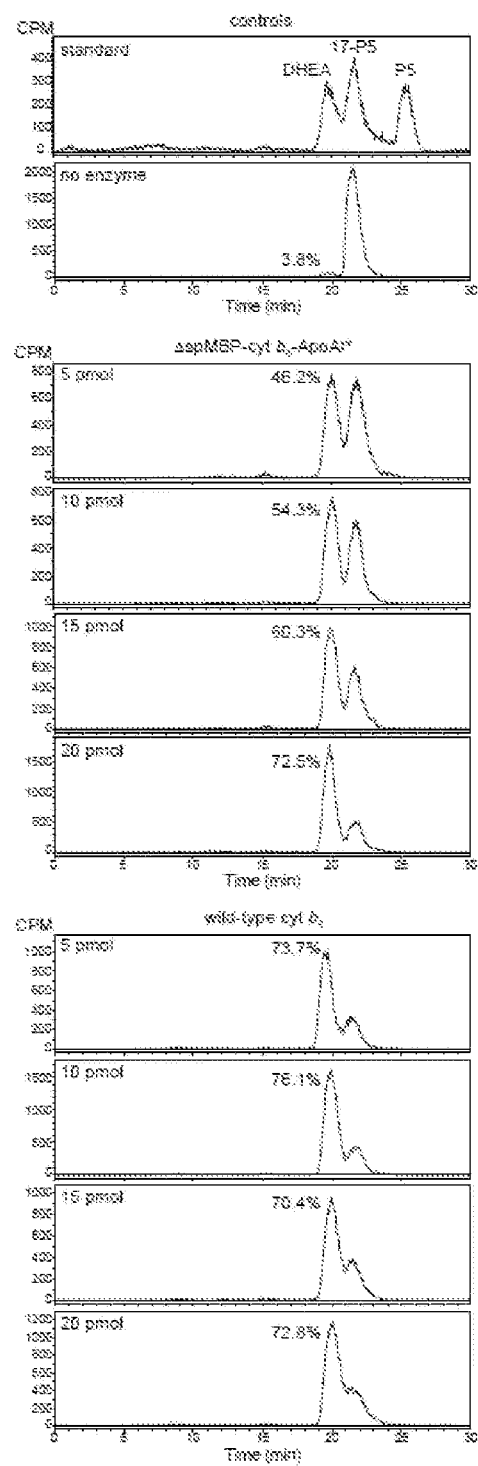

FIGS. 9A-9B show solubilization of cyt b5 using SIMPLEx. FIG. 9A shows a schematic of the steroidogenesis pathway. CYP17A1 has two distinct activities: 17-hydroxylase activity is critical in cortisol synthesis, whereas 17,20-lyase activity generates sex steroid precursors. The production of dehydroepiandrosterone (DHEA) by CYP17A1, from its precursor 17-hydroxypregnenolone (17-P5), is stimulated by cyt b5. i. P450 cholesterol side-chain cleavage (P450scc); ii. 3-hydroxysteroid dehydrogenase, Δ4,5-isomerase; iii. CYP17A1 (OHase); iv. CYP17A1 (lyase); v. 17β-hydroxysteroid dehydrogenase; vi. 5α-reductase; vii. aromatase (CYP19). FIG. 9B shows HPLC chromatograms of products formed upon incubation of human CYP17A1 with 17-P5 in the presence of human cyt b5. Chromatographic mobility of DHEA, 17-P5 and pregnenolone (P5) standards are shown in top panel followed by a typical reaction in the absence of cyt b5. Incubation of human CYP17A1 with increasing concentrations of ΔspMBP-cyt b5-ApoAI* or in the presence of wildtype cyt b5 are shown in the next set of panels. Chromatograms show substrate and product concentrations, measured as counts per minute (CPM), as a function of retention times.

Figure 10A:
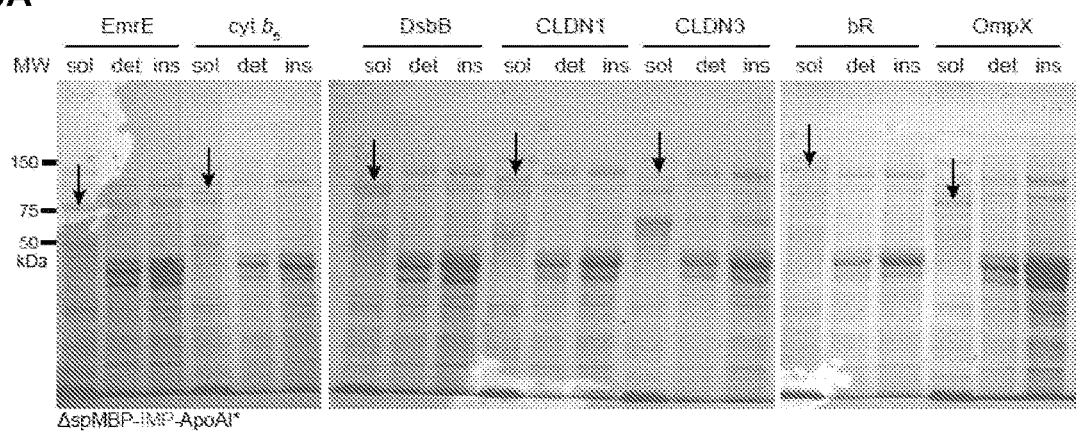
Figure 10B:
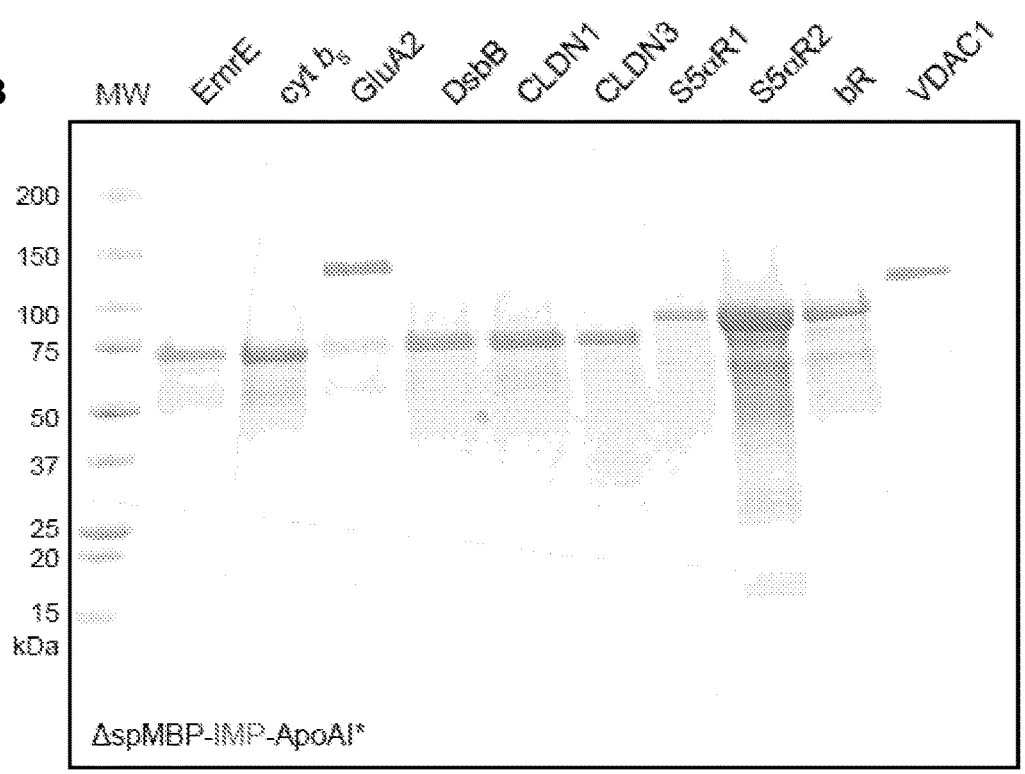

FIGS. 10A-10B show in vivo solubilization of structurally diverse IMP targets. FIG. 10A shows Coomassie stained gels of soluble (sol), detergent solubilized (det), and insoluble (ins) fractions derived from *E. coli* strain BL21 (DE3) expressing representative ΔspMBP-IMP-ApoAI* fusions corresponding to the indicated IMPs. Molecular weight (MW) markers are shown on the left. FIG. 10B shows a Coomassie stained gel of purified fractions derived from *E. coli* strain BL21(DE3) expressing representative spMBP-IMP-ApoAI* fusions corresponding to the indicated IMPs. Molecular weight (MW) ladder is shown on the left.

FIGS. 11A-11B illustrate negative staining electron microscopy of solubilized EmrE. FIG. 11A shows electron microscopy imaging by negative staining of purified OspA-EmrE-ApoAI* protein (0.1 mg/mL) prepared over 300- mesh carbon coated discs. The scale bar corresponds to 50 nm. FIG. 11B shows amplification (5×) of OspA-EmrE-ApoAI* molecules from FIG. 11A generated using ImageJ software.

FIGS. 12A-12F show dynamic light scattering of SEC-purified OspA-EmrE-ApoAI*. FIGS. 12A-12C show dimeric OspA-EmrE-ApoAI* was incubated with 1 μM ethidium bromide (EtBr) and its size was monitored 5 min (FIG. 12B) and 15 min (FIG. 12C) after the mixing and compared to OspA-EmrE-ApoAI* in the absence of EtBr (FIG. 12A). FIGS. 12D-12F show that SEC-purified tetrameric OspA-EmrE-ApoAI* was incubated with 10 mM CHAPS (cmc 6-10 mM), a nondenaturing zwitterionic detergent for solubilizing membrane proteins and breaking protein-protein interactions. The distribution of protein size in solution was measured 15 min (FIG. 12E) and 60 min (FIG. 12F) after mixing and compared to tetrameric OspA-EmrE-ApoAI* in buffer without CHAPS (FIG. 12D). The y-axis represents the relative percentage of particles (mass %) of the total population of molecules in solution that exhibit a given radius (x-axis, in nm).

Figure 13A:
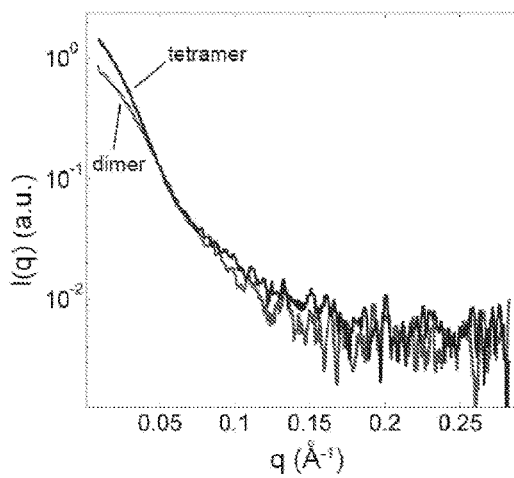
Figure 13B:
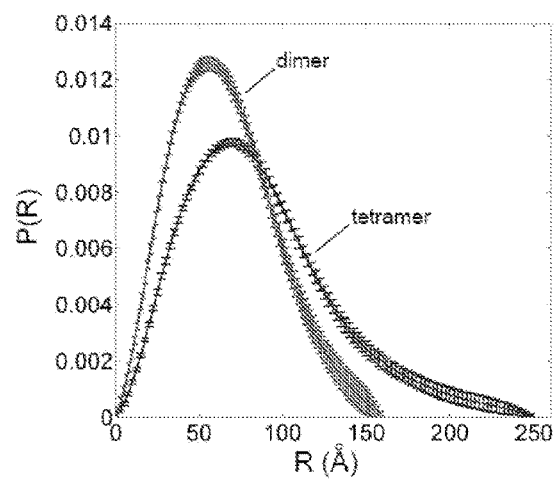
Figure 13C:
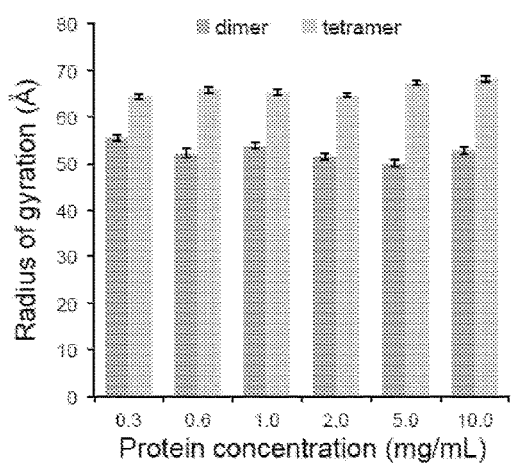
Figure 13D:
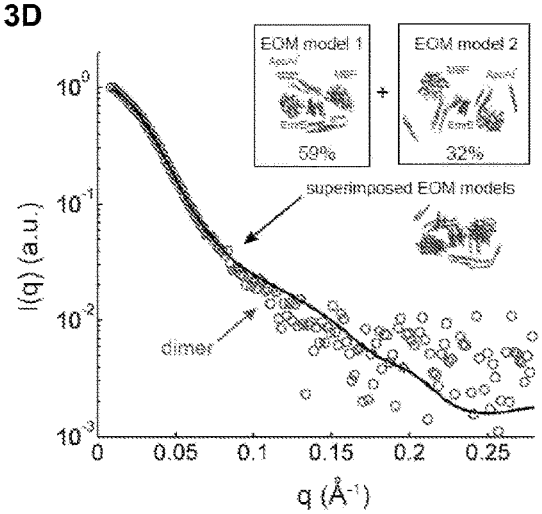

FIGS. 13A-13D show analysis of SAXS data for ΔspMBP-EmrE-ApoAI*. FIG. 13A show scattering intensity I(q) as a function of the scattering vector q measured at 1 mg/mL for both dimer and tetramer. The molecular mass is proportional to I(0), the extrapolated scattering intensity at zero scattering angle, hence the I(0) of ΔspMBP-EmrEApoAI* tetramer (1.6120±0.0432) is nearly a factor of two of that of the dimer (0.8323±0.0225). FIG. 13B shows that the pair distance distribution function P(R) calculated by GNOM provides information about the particle shape and dimensions. The data demonstrates the differences in both the correlation length (peak position) and Dmax (maximum dimension) between the dimeric (red) and tetrameric (blue) forms of ΔspMBP-EmrE-ApoAI*. FIG. 13C shows the radius of gyration for dimeric and tetrameric ΔspMBP-EmrE-ApoAI* species plotted as a function of protein concentration. The radius of gyration (the root mean square distance between the electrons within the particle) is the first-order structural parameter determined from the SAXS data, yielding direct information about the particle size. When a protein aggregates (e.g., as a result of protein concentration), the radius of gyration increases. The results indicate that even at 10 mg/mL, ΔspMBP-EmrE-ApoAI* retains the radius of gyration observed at more dilute concentrations. FIG. 13D shows an EOM fit to the scattering profile for ΔspMBP-EmrE-ApoAI* dimer. An ensemble containing three models was selected by EOM from a pool of 10,000 potential dimer structures to represent the experimental data (circles). The two most populated models are shown inside the boxes along with their percentage populations. The averaged theoretical scattering profile of the ensemble (solid line) was plotted against the dimer data, demonstrating good agreement ($\chi 2=0.250$). The superimposed models show that ApoAI proteins tend to wrap around the EmrE dimer while ΔspMBP lines up on the opposite sides of EmrE-ApoAI*.

Figure 14:
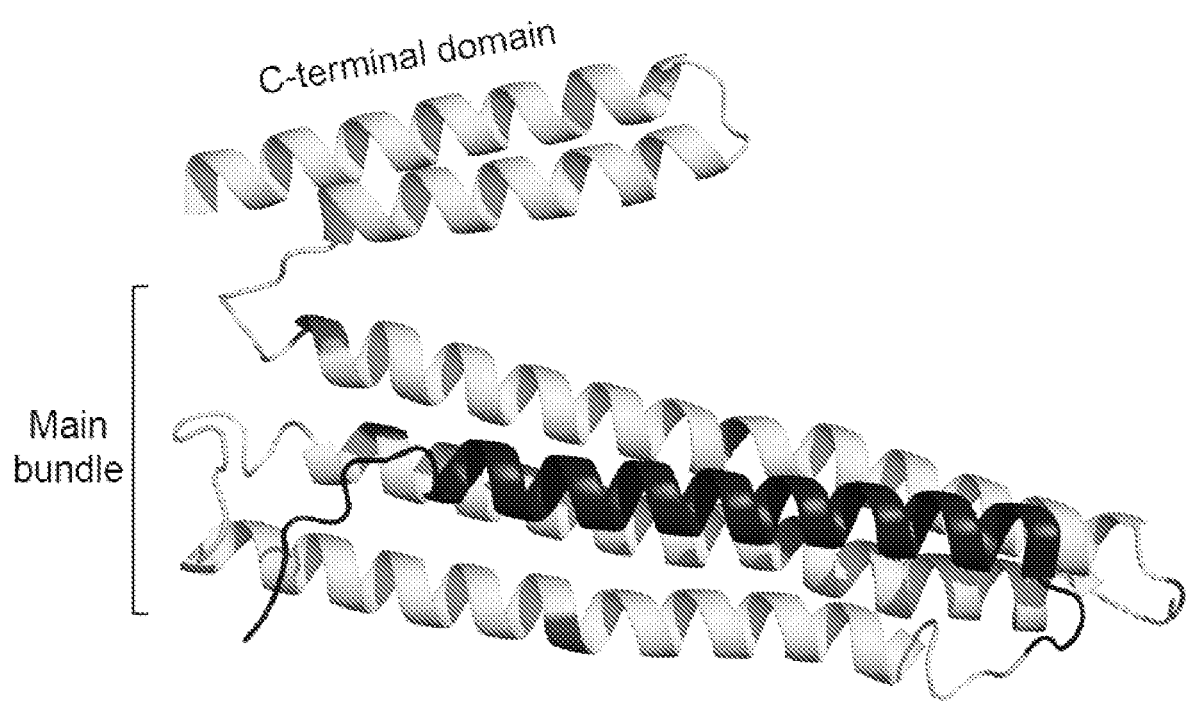

FIG. 14 shows the crystal structure of full-length ApoAI in lipid-free conformation. The ApoAI structure (Ajees et al., "Crystal Structure of Human Apolipoprotein A-I: Insights into its Protective Effect Against Cardiovascular Diseases," *Proc. Natl. Acad. Sci. U.S.A.* 103:2126-31 (2006), which is hereby incorporated by reference in its entirety) is composed of two helical domains: the main bundle and the C-terminal domain. The first 43 amino acids (blue helix) are not part of the lipid-binding domain (yellow helices). Highlighted are the residues (prolines and glycines) that in the absence of the N-terminal helix are responsible for breaking the helical structure and providing flexibility such that the structure can more easily interact with hydrophobic chains of lipids. This characteristic has been employed in the formation of nanodiscs.

DETAILED DESCRIPTION OF THE INVENTION

A first aspect of the present invention relates to a nucleic acid construct. The construct includes a chimeric nucleic acid molecule comprising a first nucleic acid moiety encoding an amphipathic shield domain protein; a second nucleic acid moiety encoding an integral membrane protein; and a third nucleic acid moiety encoding a water soluble expression decoy protein. The first nucleic acid moiety is coupled to the second nucleic acid moiety's C-terminus and the third nucleic acid moiety is coupled to the second nucleic acid moiety's N-terminus. The coupling may be direct or indirect.

Another aspect of the present invention relates to a chimeric protein. The chimeric protein includes an amphipathic shield domain protein moiety; an integral membrane protein moiety; and a water soluble expression decoy protein moiety. The amphipathic shield protein moiety is coupled to the integral membrane protein moiety's C-terminal domain and the water soluble expression decoy protein moiety is coupled to the integral membrane protein moiety's N-terminal domain.

The nucleic acid molecules encoding the various polypeptide components of a chimeric protein can be ligated together along with appropriate regulatory elements that provide for expression of the chimeric protein. Typically, the nucleic acid construct encoding the chimeric protein can be inserted into any of the many available expression vectors and cell systems using reagents that are well known in the art and further described infra.

As used herein, "nucleic acid", refers to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The nucleic acid construct may be a synthetic nucleic acid construct. As used herein "synthetic" nucleic acid construct refers to a nucleic acid construct that is artificially produced and/or that does not exist in nature. As described in more detail herein, the nucleic acid constructs and chimeric protein of the present invention are utilized to make water-soluble IMPs in vivo using an amphipathic protein fusion strategy. In particular, the nucleic acid constructs and chimeric protein are part of a new strategy for the solubilization of IMPs based on the affinity for hydrophobic surfaces displayed by amphipathic proteins. This affinity was exploited to create specific protein-protein interactions in vivo between an amphipathic protein and a given IMP.

As used herein, the term "integral membrane protein" (IMP) includes a type of transmembrane protein held in the bilayer of a cellular membrane by lipid groups with tight binding to other proteins. The IMPs of the present invention play vital roles in all cells including intra- and intercellular communication and molecular transport. The IMPs of the present invention are uniquely stable and water soluble following extraction from their native environment (e.g., a cellular membrane) without the use of detergents and/or detergent-like amphiphiles, overproduction using recombinant systems, protein engineering, and/or mutations to the IMP itself, thereby allowing for improved functional and structural studies of IMPs as well as in vitro reconstitution of enzymatic activity or in vitro reconstitution of a biological pathway involving water soluble IMP enzymes and engineering of biological/metabolic pathways directly in living cells involving the water soluble IMPs.

The IMPs of the present invention may be selected from the group consisting of bitopic α-helical IMPs, polytopic α-helical IMPs, IMPs with multiple helices, and polytopic β-barrel IMPs. The IMPs of the present invention may be classified structurally as β-barrel or α-helical bundles. β-barrels may be expressed as inclusion bodies, purified and refolded for structural studies, whereas α-helical bundles are less likely to produce soluble active forms after refolding.

In one embodiment, the bitopic α-helical IMP is human cytochrome b5 (cyt $b_5$). Cyt $b_5$ is a 134-residue bitopic membrane protein consisting of six α-helices and five β-strands folded into three distinct domains: (i) an N-terminal haeme-containing soluble domain; (ii) a C-terminal membrane anchor; and (iii) a linker or hinge region that connects the two domains. Native cyt $b_5$ stimulates the 17,20-lyase activity of cytochrome P450c17 (17α-hydroxylase/17,20-lyase; CYP17A1). In particular, a molar equivalent of cyt $b_5$ increases the rate of the 17,20-lyase reaction 10-fold, via an allosteric mechanism that does not require electron transfer. Given that the C-terminal transmembrane helix of cyt $b_5$ is required to stimulate the 17,20-lyase activity of human CYP17A1, the ApoAI* shield may, in one embodiment, be sufficiently flexible to allow the protein-protein interactions that are necessary to promote proper function.

In another embodiment, the polytopic α-helical IMP is selected from the group consisting of Homo sapiens hydroxy steroid dehydrogenase (HSD17β3), H. sapiens glutamate receptor A2 (GluA2), E. coli DsbB (DsbB), H. sapiens Claudin1 (CLDN1), H. sapiens Claudin3 (CLDN3), H. sapiens sapiens steroid 5a-reductase type 1 (S5αR1), H. sapiens sapiens steroid 5a-reductase type 2 (S5αR2), and Halobacterium sp. NRC-1 bacteriorhodopsin (bR). In one embodiment, a small (110 amino acids) polytopic α-helical IMP from E. coli named ethidium multidrug resistance protein E (EmrE), comprised of four transmembrane α-helices having 18-22 residues per helix with very short extramembrane loops, may be used. EmrE as described herein is the archetypical member of the small multidrug resistance protein family in bacteria and confers host resistance to a wide assortment of toxic quaternary cation compounds by secondary active efflux.

In another embodiment, the polytopic β-barrel IMP is selected from the group consisting of E. coli OmpX (OmpX) and Rattus norvegicus voltage-dependent anion channel 1 (VDAC1).

In another embodiment, the IMPs with multiple helices may further include, for example, polytopic β-barrel membrane proteins such as outer membrane proteins including, for example, OmpX, OmpX$^a$, OmpA, OmpA$^a$, PagP$^a$, NspA, OmpT, OpcA, NalP, OmpLA, TolC, FadL, OmpF, PhoE, Porin, OmpK36, Omp32, MspA, LamB, Maltoporin, ScrY, BtuB, FhuA, FepA, and FecA. See Tamm et al., "Folding and Assembly of β-barrel Membrane Proteins," Biochimica et Biophysica Acta 1666:250-263 (2004), which is hereby incorporated by reference in its entirety. Non-constitutive β-barrel membrane proteins include, but are not limited to, α-Hemolysin and LukF. See Tamm et al., "Folding and Assembly of β-barrel Membrane Proteins," Biochimica et Biophysica Acta 1666:250-263 (2004), which is hereby incorporated by reference in its entirety.

In yet another embodiment, the IMP is selected from the group consisting of G protein-coupled receptors (GPCR) and olfactory receptors. GPCRs can include the Class A (Rhodopsin-like) GPCRs, which bind amines, peptides, hormone proteins, rhodopsin, olfactory prostanoid, nucleotide-like compounds, cannabinoids, platelet activating factor, gonadotropin-releasing hormone, thyrotropin-releasing hormone and secretagogue, melatonin and lysosphingolipid and LPA. GPCRs with amine ligands can include, without limitation, acetylcholine or muscarinic, adrenoceptors, dopamine, histamine, serotonin or octopamine receptors); peptide ligands include but are not limited to angiotensin, bombesin, bradykinin, anaphylatoxin, Fmet-leu-phe, interleukin-8, chemokine, cholecystokinin, endothelin, melanocortin, neuropeptide Y, neurotensin, opioid, somatostatin, tachykinin, thrombin vasopressin-like, galanin, proteinase activated, orexin and neuropeptide FF, adrenomedullin (G10D), GPR37/endothelin B-like, chemokine receptor-like and neuromedin U.

Ligands of other specific GPCRs include hormone protein, rhodopsin, olfactory, prostanoid, nucleotide-like (adenosine, purinoceptors), cannabinoid, platelet activating factor, gonadotropin-releasing hormone, thyrotropin-releasing hormone & secretagogue, melatonin and lysosphingolipid & LPA, among others. Class B secretin-like GPCRs include, without limitation, those which bind calcitonin, corticotropin releasing factor, gastric inhibitory peptide, glucagon, growth hormone-releasing hormone, parathyroid hormone, PACAP, secretin, vasoactive intestinal polypeptide, diuretic hormone, EMR1 and latrophilin. Class C metabotropic glutamate receptors include those which bind metabotropic glutamate, extracellular calcium-sensing or GABA-B, among others. See U.S. Pat. No. 7,662,410 to Sligar et al. which is hereby incorporated by reference in its entirety.

As used herein, the term "amphipathic shield domain protein" includes any protein that displays both hydrophilic and hydrophobic surfaces and is often associated with lipids as membrane anchors or involved in their transport as soluble particles. The amphipathic shield domain protein, in one embodiment, serves as a molecular shield to sequester large lipophilic surfaces of the IMP from water.

In various other embodiments, the amphipathic shield domain protein is selected from the group consisting of apolipoprotein A (ApoA), apolipoprotein B (ApoB), apolipoprotein C (ApoC), apolipoprotein D (ApoD), apolipoprotein E (ApoE), apolipoprotein H (ApoH), and a peptide self-assembly mimic (PSAM). In particular, the amphipathic shield domain protein may be apolipoprotein A1 (ApoAI). As used herein, ApoAI avidly binds phospholipid molecules and organizes them into soluble bilayer structures or discs that readily accept cholesterol. ApoAI contains a globular amino-terminal (N-terminal) domain (residues 1-43) and a lipid-binding carboxyl-terminal (C-terminal) domain (residues 44-243). In one embodiment, the ApoAI may be truncated (ApoAI*). Truncated variants of ApoA1 include, but are not limited to, human ApoAI lacking its 43-residue globular N-terminal domain. As used herein, ApoA1 exhibits remarkable structural flexibility, and may adopt a molten globular-like state for lipid-free ApoAI under conditions that may allow it to adapt to the significant geometry changes of the lipids with which it interacts. The present invention designs chimeras in which, for example, ApoAI* may be genetically fused to the C terminus of an IMP target. Expression of these chimeras in the cytoplasm of Escherichia coli may yield appreciable amounts of globular, water-soluble IMPs that are stabilized in a hydrophobic environment and retain structurally relevant conformations. The approach provides, inter alia, a facile method for efficiently solubilizing structurally diverse IMPs, for example in both bacteria and human cells, as a prelude to functional and structural studies, all without the need for detergents or lipid reconstitutions. In one embodiment, a plasmid may be used which encodes a chimeric protein in which ApoAI is fused to the C-terminus of EmrE. In another embodiment, the amphipathic shield domain protein is a peptide self-assembly mimic (PSAM).

As used herein, the term "water soluble expression decoy protein" includes any protein which serves to direct an IMP into cellular cytoplasm. The water soluble expression decoy protein may assist in "tricking" a hydrophobic IMP into thinking that it is not hydrophobic. The water soluble expression decoy protein may include, for example, a protein from *Borrelia burgdorferi*, namely outer surface protein A (OspA), which is lacking its native export signal peptide. In one embodiment, the OspA may be introduced to the N terminus of chimeric nucleic acid construct of the IMP and the amphipathic shield domain protein described herein (e.g., an EmrE-ApoAI* chimera). In one embodiment, the nucleic acid molecule may encode for a chimeric protein containing a fusion of OspA-EmrE-ApoAI. In such an embodiment, the majority of the soluble OspA-EmrE-ApoAI fusion may be dimers and tetramers and may also include a dimer or dimers. The importance of the decoy can be shown by an EmrE-ApoAI* fusion lacking the OspA decoy, in which accumulation in the detergent soluble and insoluble fractions occurs in a manner similar to EmrE expressed alone. This insolubility is largely due to EmrE as the ApoAI* domain expressed on its own accumulated in all three fractions of the lysate. The water soluble expression decoy protein may alternatively be, but is not limited to, maltose binding protein (MBP) lacking its native export signal peptide, DnaB lacking its native export signal peptide, green fluorescent protein (GFP), and glutathione S-transferase (GST). MBP is highly soluble and larger than OspA and in one embodiment, may be positioned at the N-terminal of the chimeric nucleic acid molecule and/or protein of the present invention. The chimeric nucleic acid molecule may encode for a chimeric protein containing a fusion of MBP-EmrE-ApoAI. Moreover, the N-terminal domain may be removed by proteolytic digestion, resulting in an IMP-ApoAI* cleavage product which remains soluble. Together these results suggest that the N-terminal domain functions to direct folding away from the membrane while the ApoAI* domain promotes water solubility. The solubilization of IMPs by ApoAI* may be due to protein-protein interactions. A GFP domain may be added to the C terminus of the construct. The EmrE component of the fusion construct may also be modified at its N terminus with the archetypal twin-arginine translocation (Tat) export signal from *E. coli* trimethylamine N-oxide reductase (spTorA), forming a spTorA-OspA-EmrE-ApoAI* construct. This 39-residue signal peptide bears a canonical twin-arginine motif (S/T-R-R-X-F-L-K) and has been extensively used to target structurally diverse recombinant proteins for proofreading by the Tat translocase. DeLisa et al., "Folding Quality Control in the Export of Proteins by the Bacterial Twin-Arginine Translocation Pathway," *Proc. Natl. Acad. Sci. U.S.A.* 100:6115-20 (2003) and Fisher et al., "Genetic Selection for Protein Solubility Enabled by the Folding Quality Control Feature of the Twin-Arginine Translocation Pathway," *Protein Sci.* 15:449-58 (2006), both of which are hereby incorporated by reference in their entirety.

In one embodiment, the construct further includes a promoter and a termination sequence, wherein the promoter and the termination sequence are operatively coupled to the chimeric nucleic acid molecule.

The nucleic acid molecules of the present invention refer to the polymeric form of nucleotides of at least 10 bases in length. These include DNA molecules (e.g., linear, circular, cDNA, chromosomal, genomic, or synthetic, double stranded, single stranded, triple-stranded, quadruplexed, partially double-stranded, branched, hair-pinned, circular, or in a padlocked conformation) and RNA molecules (e.g., tRNA, rRNA, mRNA, genomic, or synthetic) and analogs of the DNA or RNA molecules of the described as well as analogs of DNA or RNA containing non-natural nucleotide analogs, non-native inter-nucleoside bonds, or both. The isolated nucleic acid molecule of the invention includes a nucleic acid molecule free of naturally flanking sequences (i.e., sequences located at the 5' and 3' ends of the nucleic acid molecule) in the chromosomal DNA of the organism from which the nucleic acid is derived. In various embodiments, an isolated nucleic acid molecule can contain less than about 10 kb, 5 kb, 4 kb, 3 kb, 2 kb, 1 kb, 0.5 kb, 0.1 kb, 50 bp, 25 bp or 10 bp of naturally flanking nucleotide chromosomal DNA sequences of the microorganism from which the nucleic acid molecule is derived.

Chimeric proteins of the present invention include a continuous polymer of amino acids which comprise the full or partial sequence of two or more distinct proteins. The construction of chimeric and/or fusion proteins is well-known in the art. Two or more amino acids sequences may be joined chemically, for instance, through the intermediacy of a crosslinking agent. For example, a chimeric or fusion protein may be generated by expression of a chimeric or fusion gene construct in a host cell. Chimeric and fusion gene constructs generally also contain replication origins active in host cells and one or more selectable markers encoding, for example, drug or antibiotic resistance. The present invention is also directed to plasmids containing expression system constructed to express chimeric proteins, described supra, of the present invention. The invention is also concerned with host cells that contain plasmids having the sequences of the above-described expression systems.

The chimeric and/or fusion proteins of the present invention can be generated as described herein or using any other standard technique known in the art. For example, the chimeric and/or fusion polypeptide can be prepared by translation of an in-frame fusion of the polynucleotide sequences, i.e., a hybrid gene. The hybrid gene encoding the fusion polypeptide is inserted into an expression vector which is used to transform or transfect a host cell. In one embodiment, the first nucleic acid moiety or amphipathic shield domain protein moiety may be coupled to the second nucleic acid moiety's or the IMP moiety's C-terminus, and the third nucleic acid moiety or water soluble expression decoy protein moiety may be coupled to the second nucleic acid moiety's or IMP moiety's N-terminus.

Different chimeric or fusion gene constructs encoding unique chimeric fusion proteins may be present on separate nucleic acid molecules or on the same nucleic acid molecule. Inclusion of different chimeric or fusion gene constructs on the same nucleic acid molecule is advantageous, in that uptake of only a single species of nucleic acid by a host cell is sufficient to introduce sequences encoding the amphipathic shield domain protein, IMP, and/or water soluble expression decoy protein into the host cell. By contrast, when different chimeric or fusion constructs are present on different nucleic acid molecules, both nucleic acid molecules are taken up by a particular host cell for the assay to be functional.

Once the chimeric or fusion protein is identified, the nucleic acid construct encoding the protein is inserted into an expression system to which the molecule is heterologous. The heterologous nucleic acid molecule is inserted into the expression system or vector in proper sense (5'→3') orientation relative to the promoter and any other 5' regulatory molecules, and correct reading frame. The preparation of the nucleic acid constructs can be carried out using standard cloning methods well known in the art as described by Sambrook et al., Molecular Cloning: *A Laboratory Manual*, Cold Springs Laboratory Press, Cold Springs Harbor, New York (1989), which is hereby incorporated by reference in its entirety. U.S. Pat. No. 4,237,224 to Cohen and Boyer, which is hereby incorporated by reference in its entirety, also describes the production of expression systems in the form of recombinant plasmids using restriction enzyme cleavage and ligation with DNA ligase.

A variety of prokaryotic expression systems can be used to express the fusion proteins of the present invention. Expression vectors can be constructed which contain a promoter to direct transcription, a ribosome binding site, and a transcriptional terminator. Examples of regulatory regions suitable for this purpose in *E. coli* are the promoter and operator region of the *E. coli* tryptophan biosynthetic pathway (Yanofsky et al., "Repression is Relieved Before Attenuation in the trp Operon of *Escherichia coli* as Tryptophan Starvation Becomes Increasingly Severe," *J. Bacteria.* 158:1018-1024 (1984), which is hereby incorporated by reference in its entirety) and the leftward promoter of phage lambda (N) (Herskowitz et al., "The Lysis-lysogeny Decision of Phage Lambda: Explicit Programming and Responsiveness," *Ann. Rev. Genet.*, 14:399-445 (1980), which is incorporated by reference in its entirety). Vectors used for expressing foreign genes in bacterial hosts generally will contain a sequence for a promoter which functions in the host cell. Plasmids useful for transforming bacteria include pBR322 (Bolivar et al., "Construction and Characterization of New Cloning Vehicles II. A Multipurpose Cloning System," *Gene* 2:95-113 (1977), which is hereby incorporated by reference in its entirety), the pUC plasmids (Messing, "New M13 Vectors for Cloning," *Meth. Enzymol.* 101:20-77 (1983), Vieira et al., "New pUC-derived Cloning Vectors with Different Selectable Markers and DNA Replication Origins," *Gene* 19:259-268 (1982) which are hereby incorporated by reference in their entirety), and derivatives thereof. Plasmids may contain both viral and bacterial elements. Methods for the recovery of the proteins in biologically active form are discussed in U.S. Pat. No. 4,966,963 to Patroni and U.S. Pat. No. 4,999,422 to Galliher, which are incorporated herein by reference in their entirety. Suitable expression vectors include those which contain replicon and control sequences that are derived from species compatible with the host cell. For example, if *E. coli* is used as a host cell, plasmids such as pUC19, pUC18 or pBR322 may be used. Alternatively, plasmids such as pET28a and pMALc2× may be used. Other suitable expression vectors are described in *Molecular Cloning: a Laboratory Manual:* 3rd edition, Sambrook and Russell, 2001, Cold Spring Harbor Laboratory Press, which is hereby incorporated by reference in its entirety. Many known techniques and protocols for manipulation of nucleic acids, for example in preparation of nucleic acid constructs, mutagenesis, sequencing, introduction of DNA into cells and gene expression, and analysis of proteins, are described in detail in *Current Protocols in Molecular Biology*, Ausubel et al. eds., (1992), which is hereby incorporated by reference in its entirety.

Different genetic signals and processing events control many levels of gene expression (e.g., DNA transcription and messenger RNA ("mRNA") translation) and subsequently the amount of fusion protein that is displayed on the ribosome surface. Transcription of DNA is dependent upon the presence of a promoter, which is a DNA sequence that directs the binding of RNA polymerase, and thereby promotes mRNA synthesis. Promoters vary in their "strength" (i.e., their ability to promote transcription). For the purposes of expressing a cloned gene, it is desirable to use strong promoters to obtain a high level of transcription and, hence, expression and surface display. Therefore, depending upon the host system utilized, any one of a number of suitable promoters may also be incorporated into the expression vector carrying the deoxyribonucleic acid molecule encoding the protein of interest coupled to a stall sequence. For instance, when using *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Translation of mRNA in prokaryotes depends upon the presence of the proper prokaryotic signals, which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, "Maximizing Gene Expression on a Plasmid Using Recombination In Vitro," *Methods in Enzymology* 68:473-82 (1979), which is hereby incorporated by reference in its entirety.

In accordance with this and other aspects of the present invention, the amphipathic shield domain protein, IMP, and/or water soluble expression decoy proteins may be connected in the presence or absence of a ligand. As used herein, the term "ligand" refers to a substance that is able to bind to and form transient or stable complexes with a protein, molecule, chimeric molecule, ligand (dimer), substrate (dimer), a second substrate, a second ligand, target domain, regions, portions, and fragments thereof, and the like, to serve a biological purpose, for example a ligand which interacts with an enzyme in the process of an enzymatic reaction. Ligands also include signal triggering molecules which bind to sites on a target protein, by intermolecular forces such as ionic bonds, hydrogen bonds and Van der Waals forces. Useful ligands include, for example, ethidium bromide (EtBr), methyl viologen (MV) and tetraphenylphosphonium (TPP$^+$), monotopic membrane proteins, polytopic membrane proteins, transmembrane proteins, G protein-coupled receptors (GPCRs), ion channels, members of the SNARE protein family, integrin adhesion receptor, multi-drug efflux transporters.

In accordance with this and other aspects of the present invention, the amphipathic shield domain protein, IMP, and/or water soluble expression decoy proteins are linked either directly or via a linker located adjacent to each other within the construct, coupled to each other in tandem or separated by at least one linker. In one embodiment, the chimeric nucleic acid molecule or chimeric protein includes a linker coupling the nucleic acid or protein moieties together. The proteins may be linked by a covalent linkage or may be linked by methods known in the art for linking peptides. In one embodiment, the chimeric protein may further include one or more linker moieties coupling said amphipathic shield domain protein, IMP, and/or water soluble expression decoy protein moieties together, consistent with those described in previous aspects of the invention. In one embodiment, the chimeric protein is in water soluble form, as described above.

Linkers may include synthetic sequences of amino acids that are commonly used to physically connect polypeptide domains to each other or to biologically relevant moieties. Most linker peptides are composed of repetitive modules of one or more of the amino acids glycine and serine. Peptide linkers have been well-characterized and shown to adopt unstructured, flexible conformations. For example, linkers comprised of Gly and Ser amino acids have been found to not interfere with assembly and binding activity of the domains it connects. Freund et al., "Characterization of the Linker Peptide of the Single-chain Fv Fragment of an Antibody by NMR Spectroscopy," *FEBS* 320:97 (1993), which is hereby incorporated by reference in its entirety.

The nucleic acid construct and chimeric protein of the present invention may include a flexible polypeptide linker separating the amphipathic shield domain protein, IMP, and/or water soluble expression decoy proteins and allowing for their independent folding. The linker is optimally 15 amino acids or 60 Å in length (~4 Å per residue) but may be as long as 30 amino acids but preferably not more than 20 amino acids in length. It may be as short as 3 amino acids in length, but more preferably is at least 6 amino acids in length. To ensure flexibility and to avoid introducing steric hindrance that may interfere with the independent folding of the fragment domain of reporter protein and the members of the putative binding pair, the linker should be comprised of small, preferably neutral residues such as Gly, Ala, and Val, but also may include polar residues that have heteroatoms such as Ser and Met, and may also contain charged residues. The first, second, and third proteins may be linked via a short polypeptide linker sequence. Suitable linkers include peptides of between about 2 and about 40 amino acids in length and may include, for example, glycine residues Gly185 and Gly186. Preferred linker sequences include glycine-rich (e.g. $G_{3-5}$), serine-rich (e.g. GSG, GSGS (SEQ ID NO: 1), GSGSG (SEQ ID NO: 2), $GS_NG$), or alanine rich (e.g., TSAAA (SEQ ID NO: 3)) linker sequences. Other exemplary linker sequences have a combination of glycine, alanine, proline and methionine residues such as AAAGGM (SEQ ID NO: 4); AAAGGMPPAAAGGM (SEQ ID NO: 5); AAAGGM (SEQ ID NO: 6); and PPAAAGGMM (SEQ ID NO: 7). Linkers may have virtually any sequence that results in a generally flexible chimeric protein.

Another aspect of the invention relates to an expression vector including the nucleic acid construct of the present invention. Suitable nucleic acid vectors include, without limitation, plasmids, baculovirus vectors, bacteriophage vectors, cosmids, fosmids, bacterial artificial chromosomes, viral vectors (for example, viral vectors based on vaccinia virus, poliovirus, adenovirus, adeno-associated virus, SV40, herpes simplex virus, and the like), P1-based artificial chromosomes, yeast plasmids, yeast artificial chromosomes, and other vectors. In some embodiments of the present invention, vectors suitable for use in prokaryotic host cells. Accordingly, exemplary vectors for use in prokaryotes such as *Escherichia coli* include, but are not limited to, pACYC184, pBeloBac11, pBR332, pBAD33, pBBR1MCS and its derivatives, pSC101, SuperCos (cosmid), pWE15 (cosmid), pTrc99A, pBAD24, vectors containing a ColE1 origin of replication and its derivatives, pUC, pBluescript, pGEM, and pTZ vectors.

Another aspect of the present invention relates to a host cell comprising the nucleic acid construct of the present invention. In accordance with this and other aspects of the present invention, suitable host cells include both eukaryotic and prokaryotic cells. In one embodiment, the host cell is a eukaryote. Eukaryotic host cells, include without limitation, animal cells, fungal cells, insect cells, plant cells, and algal cells. Suitable eukaryotic host cells include, but are not limited to, *Pichia pastoris, Pichia finlandica, Pichia trehalophila, Pichia koclamae, Pichia membranaefaciens, Pichia opuntiae, Pichia thennotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorphs, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii,* and the like.

In accordance with the present invention, the host cell may be a prokaryote, such as a bacterial cell. Such cells serve as a host for expression of recombinant proteins for production of recombinant therapeutic proteins of interest. Suitable microorganisms include *Pseudomonas* sp. such as *Pseudomonas aeruginosa, Escherichia* sp., *Escherichia coli* and other Enterobacteriaceae, *Salmonella* sp. such as *Salmonella* gastroenteritis (typhimirium), *S. typhi, S. enteriditis, Shigella* sp. such as *Shigella flexneri, S. sonnie, S. dysenteriae, Neisseria* sp. such as *Neisseria gonorrhoeae, N. meningitides, Haemophilus* sp. including *Haemophilus influenzae H. pleuropneumoniae, Pasteurella* sp. including *Pasteurella haemolytica, P. multilocida, Legionella* sp. such as *Legionella pneumophila, Treponema pallidum, T. denticola, T. orales, Borrelia burgdorferi, Borrelia* spp. *Leptospira interrogans, Klebsiella* sp. such as *Klebsiella pneumoniae, Proteus vulgaris, P. morganii, P. mirabilis, Rickettsia prowazeki, R. typhi, R. richettsii, Porphyromonas (Bacteroides) gingivalis, Chlamydia psittaci, C. pneumoniae, C. trachomatis, Campylobacter* sp. such as *Campylobacter jejuni, C. intermedis, C. fetus, Helicobacter* sp. such as *Helicobacter pylori, Francisella* sp. such as *Francisella tularenisis, Vibrio cholerae, Vibrio parahaemolyticus, Bordetella* sp. including *Bordetella pertussis, Burkholderia* sp. such as *Burkholderie pseudomallei, Brucella* sp. including *Brucella abortus, B. susi, B. melitens is, B. can is, Spirillum minus, Pseudomonas mallei, Aeromonas* sp. such as *Aeromonas hydrophile, A. salmonicida,* and *Yersinia* sp. such as *Yersinia pestis.* Additional microorganisms include *Wolinella* sp., *Desulfovibrio* sp. *Vibrio* sp., *Bacillus* sp., *Listeria* sp., *Staphylococcus* sp., *Streptococcus* sp., *Peptostreptococcus* sp., *Megasphaera* sp., *Pectinatus* sp., *Selenomonas* sp., *Zymophilus* sp., *Actinomyces* sp., *Arthrobacter* sp., *Frankia* sp., *Micromonospora* sp., *Nocardia* sp., *Propionibacterium* sp., *Streptomyces* sp., *Lactobacillus* sp., *Lactococcus* sp., *Leuconostoc* sp., *Pediococcus* sp., *Acetobacterium* sp., *Eubacterium* sp., *Heliobacterium* sp.,

*Heliospirillum* sp., *Sporomusa* sp., *Spiroplasma* sp., *Ureaplasma* sp., *Erysipelothrix*, sp., *Corynebacterium* sp. *Enterococcus* sp., *Clostridium* sp., *Mycoplasma* sp., *Mycobacterium* sp., *Actinobacteria* sp., *Moraxella* sp., *Stenotrophomonas* sp., *Micrococcus* sp., *Bdellovibrio* sp., *Hemophilus* sp., *Proteus mirabilis, Enterobacter cloacae, Serratia* sp., *Citrobacter* sp., *Proteus* sp., *Acinetobacter* sp., *Actinobacillus* sp., *Capnocytophaga* sp., *Cardiobacterium* sp., *Eikenella* sp., *Kingella* sp., *Flavobacterium* sp. *Xanthomonas* sp., *Plesiomonas* sp., and alpha-proteobacteria such as *Wolbachia* sp., cyanobacteria, spirochaetes, green sulfur and green non-sulfur bacteria, Gram-negative cocci, Gram negative bacilli which are fastidious, Enterobacteriaceae-glucose-fermenting gram-negative bacilli, Gram negative bacilli-non-glucose fermenters, Gram negative bacilli—glucose fermenting, oxidase positive. Methods for transforming/transfecting host cells with expression vectors are well-known in the art and depend on the host system selected as described in Sambrook et al., Molecular Cloning: *A Laboratory Manual*, Cold Springs Laboratory Press, Cold Springs Harbor, New York (1989), which is hereby incorporated by reference in its entirety. In one embodiment, the host cell is selected from the group consisting of bacteria, yeast, and insect cells.

When the nucleic acid construct is assembled in a host cell, the host cell may be cultured in a suitable culture medium optionally supplemented with one or more additional agents, such as an inducer (e.g., where a nucleotide sequence encoding a chimeric protein is under the control of an inducible promoter). The inducer may be, for example, isopropyl-β-$_D$-thiogalactoside. In one embodiment of the present invention, a substrate is endogenous to the host cell and upon assembly of the nucleic acid construct in the host cell, the substrate is readily converted. In another embodiment, a substrate is exogenous to the host cell. In accordance with this embodiment, the culture medium is supplemented with a substrate or substrate precursor that can be readily taken up by the host cell and converted. Suitable substrates include, without limitation, proteins, nucleic acid molecules, organic compounds, lipids, and glycans.

In one embodiment of the present invention, the host cell is cultured in a suitable medium and is overlaid with an organic solvent, e.g. dodecane, forming an organic layer. In accordance with this embodiment, if the nucleic acid construct or an isolated IMP is a secreted product, the product partitions into the organic layer following production and secretion from the host cell. Subsequently, the product can be readily purified from the organic layer.

In another embodiment of the present invention, the chimeric nucleic acid construct or IMP is separated from other products, macromolecules, etc., which may be present in the cell culture medium, the cell lysate, or the organic layer. Separation of the chimeric nucleic acid construct or IMP from other products that may be present in the cell culture medium, cell lysate, or organic layer is readily achieved using standard methods known in the art, e.g., standard chromatographic techniques. Several methods are readily known in the art, including ion exchange chromatography, high performance liquid chromatography, hydrophobic interaction chromatography, affinity chromatography (e.g., $Ni^{2+}$ affinity chromatography), size exclusion chromatography, gel filtration, and reverse phase chromatography. The peptide is preferably produced in purified form (at least about 40% pure, at least about 50% pure, at least about 60% pure, at least about 70% pure, at least about 80% pure, at least about 90% pure, at least about 95% pure, at least about 98%, or more than 98% pure) by conventional techniques.

Depending on whether the recombinant host cell is made to secrete the protein into growth medium (see U.S. Pat. No. 6,596,509 to Bauer et al., which is hereby incorporated by reference in its entirety), the protein can be isolated and purified by centrifugation (to separate cellular components from supernatant containing the secreted protein) followed by sequential ammonium sulfate precipitation of the supernatant. The fraction containing the protein can be subjected to gel filtration in an appropriately sized dextran or polyacrylamide column to separate the protein from other cellular components and proteins. If necessary, the protein fraction may be further purified by HPLC. Accordingly, the chimeric nucleic acid construct or chimeric protein produced by the present invention can be used to isolate and solubilize an IMP in a purified form, e.g., "pure" in the context of an IMP or refers to an IMP that is free from other intermediate or precursor products, macromolecules, contaminants, etc.

A host cell comprising an assembled biological pathway of the present invention provides for enhanced purification and isolation of IMPs, compared to a control host cell not containing the construct. Thus, purification and isolation of IMPs is increased by at least about 10%, at least about 20%, at least about 25%, at least about 30%, at least about 40%, at least about 50%, at least about 60%, at least about 70%, at least about 80%, at least about 90%, at least about 100% (or two-fold) compared to a control host cell. In other embodiments of the present invention, the purification and isolation of IMPs is at least about 2.5-fold, at least about 3-fold, at least about 5-fold, at least about 7-fold, at least about 10-fold, at least about 15-fold, at least about 20-fold, at least about 50-fold, at least about 100-fold, or more, higher in the host cell comprising the nucleic acid construct compared to the level of the IMP produced in a control host cell.

Methods for transforming/transfecting host cells with expression vectors are well-known in the art and depend on the host system selected, as described in Sambrook et al., Molecular Cloning: *A Laboratory Manual*, Cold Springs Laboratory Press, Cold Springs Harbor, New York (1989), which is hereby incorporated by reference in its entirety. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation, and transfection using bacteriophage.

The simplest single-celled organisms are composed of central regions filled with an aqueous material and a variety of soluble small molecules and macromolecules. Enclosing this central region is a membrane which is composed of phospholipids arranged in a bilayer structure. In more complex living cells, there are internal compartments and structures that are also enclosed by membranes. There are many protein molecules embedded or associated within these membrane structures, and these membrane proteins are often the most important to determining cell functions including communication and processing of information and energy. The largest problem in studying membrane proteins is that the inside of the phospholipid bilayer is hydrophobic and the embedded or anchored part of the membrane protein is itself also hydrophobic. In isolating these membrane proteins from their native membrane environments, the present invention overcomes the difficult task of preventing IMPs from forming inactive aggregates while remaining in a native configuration. In one embodiment of the present invention, a protein is encoded by the nucleic acid construct of the present invention and, preferably, the protein is in water soluble form. The term "solubilizing" according to the present invention includes dissolving a molecule in a solution. This aspect of the invention is carried out in substantially the same way as described above.

In addition to cell-based expression hosts/systems of the present invention, water soluble IMPs of the present invention may also be expressed using cell-free expression platforms. Examples of cell-free expression platforms include, but are not limited to, the PURExpress kit from NEB and S30 lysate high-expression kit from Promega, among others.

Another aspect of the present invention relates to a chimeric nucleic acid molecule. The molecule includes a first nucleic acid moiety encoding an amphipathic shield domain protein and a second nucleic acid moiety encoding an IMP, wherein the first nucleic acid moiety is coupled directly or indirectly to the second nucleic acid moiety's C-terminus. In one embodiment, a protein is encoded by the nucleic acid molecule. This aspect of the invention is carried out in accordance with previously described aspects.

Another aspect of the present invention relates to a method of recombinantly producing an IMP in soluble form. The method includes providing the host cell of the present invention and culturing the host cell under conditions effective to express the IMP in a water soluble form within the host cell.

In one embodiment, the method further includes recovering the IMP from the host cell following the culturing. In another embodiment, the IMP is recovered from the cell's cytoplasm. The recovery of the IMP from the host cell is consistent with the recovery of proteins discussed supra. In yet another embodiment the recovering further includes lysing the cell to form a cell lysate comprising a water soluble fraction and subjecting the water soluble fraction of the cell lysate to chromatography to isolate the IMP.

In one embodiment of this aspect of the present invention, the chimeric proteins are provided in a purified isolated form. The proteins can be synthesized using standard methods of protein/peptide synthesis known in the art, including solid phase synthesis or solution phase synthesis. Alternatively, the chimeric proteins can be generated using recombinant expression systems and purified using any method readily known in the art, including ion exchange chromatography, hydrophobic interaction chromatography, affinity chromatography, gel filtration, and reverse phase chromatography. In another embodiment of the present invention, the chimeric biological pathway proteins are provided in the form of one or more nucleic acid molecules encoding the chimeric proteins, as discussed supra.

Nucleotide sequences encoding the chimeric proteins may be modified such that the nucleotide sequence reflects the codon preference for the particular host cell. For example, when yeast host cells are utilized, the nucleotide sequences encoding the chimeric proteins can be modified for yeast codon preference (see, e.g., Bennetzen and Hall, "Codon Selection in Yeast," *J. Biol. Chem.* 257(6):3026-3031 (1982), which is hereby incorporated by reference in its entirety). Likewise, when bacterial host cells are utilized, e.g., *E. coli* cells, the nucleotide sequences encoding the chimeric biological pathway proteins can be modified for *E. coli* codon preference (see e.g., Gouy and Gautier, "Codon Usage in Bacteria: Correlation With Gene Expressivity," *Nucleic Acids Res.* 10(22):7055-7074 (1982); Eyre-Walker et al., "Synonymous Codon Bias is Related to Gene Length in *Escherichia coli*: Selection for Translational Accuracy?," *Mol. Biol. Evol.* 13(6):864-872 (1996) and Nakamura et al., "Codon Usage Tabulated From International DNA Sequence Databases: Status for the year 2000," *Nucleic Acids Res.* 28(1):292 (2000), which are hereby incorporated by reference in their entirety).

A variety of genetic signals and processing events that control many levels of gene expression (e.g., DNA transcription and messenger RNA ("mRNA") translation) can be incorporated into the nucleic acid construct encoding the chimeric proteins to maximize protein production. For the purpose of expressing a cloned nucleic acid sequence encoding the desired chimeric proteins, it is advantageous to use strong promoters to obtain a high level of transcription. Depending upon the host system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted chimeric genetic construct. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR. Common promoters suitable for directing expression in a yeast cell include constitutive promoters such as an ADH1 promoter, a PGK1 promoter, an ENO promoter, a PYK1 promoter and the like; or a regulatable promoter such as a GALL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, a PGK promoter, a GAPDH promoter, an ADC1 promoter, a TRP1 promoter, a URA3 promoter, a LEU2 promoter, an ENO promoter, a TP1 promoter, and a AOX1 promoter.

There are other specific initiation signals required for efficient gene transcription and translation in eukaryotic and prokaryotic cells that can be included in the nucleic acid construct to maximize chimeric protein production. Depending on the vector system and host utilized, any number of suitable transcription and/or translation elements, including constitutive, inducible, and repressible promoters, as well as minimal 5' promoter elements, enhancers, or leader sequences may be used. For a review on maximizing gene expression see Roberts and Lauer, "Maximizing Gene Expression On a Plasmid Using Recombination In Vitro," *Methods in Enzymology* 68:473-82 (1979), which is hereby incorporated by reference in its entirety.

A nucleic acid molecule encoding a chimeric protein of the present invention, a promoter molecule of choice, including, without limitation, enhancers, and leader sequences; a suitable 3' regulatory region to allow transcription in the host, and any additional desired components, such as reporter or marker genes, are cloned into a vector of choice using standard cloning procedures in the art, such as described in Joseph Sambrook et al., MOLECULAR CLONING: A LABORATORY MANUAL (Cold Springs Harbor 1989); Frederick M. Ausubel, SHORT PROTOCOLS IN MOLECULAR BIOLOGY (Wiley 1999), and U.S. Pat. No. 4,237,224 to Cohen and Boyer, which are hereby incorporated by reference in their entirety. Suitable expression vectors include those described supra. Two or more nucleic acid molecules encoding two or more chimeric proteins can be housed in the same or different expression vectors. In one embodiment of the present invention, two or more nucleic acid molecules encoding two or more chimeric proteins are present in the same nucleic acid vector as the synthetic nucleic acid scaffold. In another embodiment of the present invention, two or more nucleic acid molecules or constructs encoding two or more chimeric biological pathway proteins are present in a different nucleic acid vector than the nucleic acid vector containing the synthetic nucleic acid scaffold.

In accordance with this embodiment of this aspect of the present invention, the system for carrying out a biological pathway further includes a host cell that houses the one or more nucleic acid vectors encoding the chimeric proteins and the nucleic acid construct. Suitable eukaryotic and prokaryotic host cells are described supra. Nucleic acid vectors encoding the chimeric proteins and containing the nucleic acid constructs can be stably or transiently introduced into a suitable host cell, using established techniques, including, but not limited to, electroporation, calcium phosphate precipitation, DEAE-dextran mediated transfection, liposome-mediated transfection, and the like. For stable transformation, a nucleic acid vector or construct will generally further include a selectable marker, e.g., any of several well-known selectable markers such as neomycin resistance, ampicillin resistance, tetracycline resistance, chloramphenicol resistance, kanamycin resistance, and the like. Stable transformation can also be effected (e.g., selected for) using a nutritional marker gene that confers prototrophy for an essential amino acid such as URA3, HIS3, LEU2, MET2, LYS2 and the like.

The nucleic acid construct may be designed to carry out a protein folding pathway, and the chimeric proteins include enzymes involved in protein folding. Enzymes involved in protein folding include, without limitation, DnaK, DnaJ, GroEL, GroES, GrpE, Trigger Factor, PspA, IbpA, IbpB, Skp, SurA, Fkbp12, Hsp104, SecB, and SRP. Enzymes involved in oxidative protein folding include, without limitation, DsbA, DsbB, DsbC, DsbD, DsbG, TrxA, TrxB, GST, Gor, AhpC, Pdi, BiP. Nucleotide and amino acid sequences of the enzymes involved in protein folding processes are well known in the art, and any known sequence can be utilized to generate chimeric proteins for use in the methods and systems of the present invention. The chimeric proteins utilized in a system to carry out protein folding can be derived from the same or different microorganism. In one embodiment, the recovered IMP is conformationally correct.

The IMP, amphipathic shield domain protein, and water soluble expression decoy protein of the present aspect is consistent with those disclosed above with respect to previous aspects. The chimeric nucleic acid molecule may further include a promoter, termination sequence, and linker nucleic acid moiety, consistent with those described in previous aspects of the invention.

As will be apparent to one of skill in the art, the present invention allows for a broad range of studies of water-soluble IMPs in vivo to be carried out quantitatively or qualitatively in eukaryotic and prokaryotic host cells. The constructs of the present invention allow for solubilized IMPs to be amenable to structural characterization including negative staining electron microscopy, dynamic light scattering and small-angle X-ray scattering (SAXS) data collection, and three-dimensional reconstruction with electron microscopy, among others.

The present invention allows for the direct expression of soluble products in living cells by simply fusing an IMP target with truncated apolipoprotein A-I, which serves as an amphipathic proteic 'shield' that sequesters the IMP from water and promotes its solubilization. The invention provides methods for determining structure and function of water soluble IMPs and allows for isolation, solubilization, and attachment of secondary particles to IMPs. The invention enables structure-function analysis of water soluble IMPs. It also allows analysis of protein-protein interactions involving the water soluble IMP. For IMPs with enzymatic function, it allows (1) in vitro reconstitution of enzymatic activity or in vitro reconstitution of a biological pathway involving the water soluble IMP enzyme; and (2) engineering of biological/metabolic pathways directly in living cells involving the water soluble IMP.

The above disclosure generally describes the present invention. A more specific description is provided below in the following examples. The examples are described solely for the purpose of illustration and are not intended to limit the scope of the present invention. Changes in form and substitution of equivalents are contemplated as circumstances suggest or render expedient. Although specific terms have been employed herein, such terms are intended in a descriptive sense and not for purposes of limitation.

EXAMPLES

Example 1—Materials and Methods

Bacterial Strains and Growth Conditions—
*E. coli* strain DH5α was used for cloning while protein expression was carried out in *E. coli* strain BL21(DE3). Overnight cultures were diluted 1:500 in terrific broth (TB) supplemented with the appropriate antibiotic (50 μg mL$^{-1}$ kanamycin or 100 μg mL$^{-1}$ ampicillin) and grown at 30° C. until culture optical density (OD$_{600}$) reached ~1.0. The temperature was then lowered to 16° C. and protein expression was induced with isopropyl-β-D-thiogalactoside (IPTG) to a final concentration of 0.1 mM. Cells were collected 20 h post induction.

Plasmid Construction—
The basic construct in these studies was a tripartite fusion between a soluble cytoplasmic decoy protein, a target IMP, and N-terminally truncated human ApoAI (Δ1-43; ApoAI*) in pET28a (Novagen). For the decoy, the N-terminal domain (residues 4-93) of the engineered outer surface protein A (OspA) of *Borrelia burgdorferi* (Makabe et al., "The Promiscuity of Beta-Strand Pairing Allows for Rational Design of Beta-Sheet Face Inversion," *J. Am. Chem. Soc.* 130: 14370-71 (2008), which is hereby incorporated by reference in its entirety) was prepared by PCR and subcloned in pET28a between the NcoI and NdeI restriction sites. This cloning resulted in an additional Gly placed immediately after Met4. As an alternative decoy for cytoplasmic expression, *E. coli* MBP lacking its N-terminal signal peptide (ΔspMBP) was used. The gene encoding ΔspMBP (residues 27-368) was subcloned from plasmid pMALc2× (New England Biolabs) in pET28a using the same restriction sites as above. This cloning resulted in an additional Gly residue immediately before Lys27 of ΔspMBP. A reverse primer introduced a triple Ala motif following Asn368 in ΔspMBP and before the NdeI site. Subsequently, ApoAI* (residues 44-243) was subcloned between EcoRI and NotI sites of the pET28a plasmid containing either OspA or ΔspMBP. The final plasmids were arranged as follows: (NcoI)-decoy protein-(NdeI)-IMP-(EcoRI)-ApoAI*-(NotI)-6×His. All IMP targets were subcloned between NdeI and EcoRI. In the absence of an IMP target, this plasmid served as the OspA-ApoAI* control. Additional control plasmids for expressing OspA-IMP/ΔspMBP-IMP (lacking ApoAI*) or unfused IMPs (lacking OspA/ΔspMBP and ApoAI*) were constructed similarly. Plasmids for fluorescence microscopy were created by introducing full-length GFP to the C-terminus of the different chimeras described above. This cloning involved ligating the gene encoding GFP between NotI and XhoI sites in each of the different pET28a plasmids described above. Plasmids for protein expression via the Tat pathway were created in plasmid pTrc99A (Pharmacia). Briefly, overlap extension PCR was used to join DNA encoding the Tat-dependent spTorA signal peptide to the 5' end of DNA encoding EmrE, OspA-EmrE, OspA-ApoAI* or OspA-EmrE-ApoAI*. During overlap extension PCR, NcoI and XbaI sites were introduced at the 5' and 3' ends, respectively, and a 6×-His tag was also introduced at the 3' end of all constructs. The resulting overlap extension PCR products were ligated into the corresponding sites in pTrc99A. All plasmids were confirmed by DNA sequencing at the Cornell Biotechnology Resource Center.

Subcellular Fractionation—

Following protein expression, 20 mL of cells expressing IMP fusions were harvested. Cultures were normalized by $OD_{600}$ and culture aliquots were pelleted via centrifugation for 10 min at 4° C. and 4,000×g. Cells were then resuspended in lysis buffer containing 30 mM Tris pH 8.0, 500 mM NaCl, and 40 mM imidazole pH 8.0 and lysed using a homogenizer (Avestin Emulsiflex C5). To separate soluble proteins from membranes, the homogenate was ultracentrifuged (100,000×g) for 1 h at 4° C. and the supernatant was collected as the soluble fraction. Detergent soluble fractions were obtained by treating the pellets resulting from the previous step with 10 mL of lysis buffer containing 2% n-dodecyl-β-D-maltoside (DDM) (Anatrace). Pellets were resuspended by douncing. Partitioning of membrane proteins into the DDM-containing lysis buffer was achieved by rotating the lysate at 4° C. for 2 h. Following ultracentrifugation (100,000×g) for 1 h at 4° C., the supernatant represented the "detergent solubilized" fraction and the pellet represented the "insoluble fraction." For experiments that involved isolation of periplasmic fractions, cells were initially resuspended in 20% sucrose, 30 mM Tris-HCl pH 8.5, 1 mM EDTA and 1 g $L^{-1}$ lysozyme and incubated at room temperature for 10 min. Following centrifugation (10 min at room temperature and 10,000×g), cell pellets were fractionated according to standard ice-cold osmotic shock. The supernatant resulting from the centrifugation step (10 min at 4° C. and 15,000×g) was taken as the periplasmic fraction, while the remaining pellet was used to prepare the soluble cytoplasmic fraction as described above. IMPs in the various fractions were separated by SDS-PAGE using 10% polyacrylamide gels (Bio-Rad) and subsequently detected by Western blotting according to standard protocols using a 1:5,000-diluted monoclonal anti-6×-His HRP-conjugated antibody (Abcam).

Protein Purification—

Proteins were purified from soluble fractions in one of two ways. For chimeras containing OspA, the supernatant containing the 6×-His-tagged protein of interest was purified using an ÄKTA Explorer FPLC system (GE Healthcare) over a $Ni^{2+}$ Sepharose High Performance HisTrap HP column (GE Healthcare). For chimeras containing ΔspMBP, purification was performed according to the manufacturer's protocol supplied with pMAL vectors (New England Biolabs). SEC was performed on all 6×-His-tagged and ΔspMBP-tagged purified proteins. Standards used to calibrate the SEC column were a lyophilized mix of thyroglobulin, bovine γ-globulin, chicken ovalbumin, equine myoglobin, and vitamin B12, MW 1,350-670,000, pI 4.5-6.9 (BioRad). Proteins were stored at a final concentration of 1 mg $mL^{-1}$ in SEC buffer (20 mM Tris pH 7.5, 50 mM NaCl, 1 mM EDTA pH 8.0) at 4° C. Expression and purification of EmrE was done according to standard protocols (Winstone et al., "Optimization of Expression and the Purification by Organic Extraction of the Integral Membrane Protein EmrE," *Protein Expr. Pur.* 26:111-21 (2002), which is hereby incorporated by reference in its entirety).

Lipid Content—

Analytical measurement of lipid content for SIMPLEx solubilized EmrE and cyt $b_5$ was performed by acid-digestion of the organic sample to produce inorganic phosphate. Subsequently, total phosphorus was measured according to standard protocols (Fiske et al., "The Colorimetric Determination of Phosphorus," *J. Biol. Chem.* 66:374-89 (1925), which is hereby incorporated by reference in its entirety).

Ligand Binding—

Fluorescence spectra of protein samples were collected using a Fluorolog-Tau-3 time-resolved spectrofluorometer (Horiba). Protein concentration of OspA-EmrE-ApoAI* in SEC buffer and EmrE in DDM containing buffer (20 mM Tris-HCl, pH 7.5, 150 mM NaCl, and 0.08% w/v DDM) was 10 μM. Fluorescence spectra using a 295-nm excitation were collected after each volume of ligand. A small magnetic stir bar was added to the 1-cm path-length quartz cuvette containing either the sample or buffer. The stirring speed was set such that the surface was not noticeably disturbed. Approximately 1 min was allowed between the addition of ligand and the beginning of spectra collection. A total of 3 replicates were performed with the first sample preparation to control for experimental variability. After this, only one experimental replicate of the following second and third sample preparations were performed. Thus, each ligand-binding curve reflects the average of 3 replicates from 3 different protein preparations to control for biological and preparation variability. A 10-nm slit width was used for both excitation and emission. The interval was set at 2.0 nm and the integration time at 0.1 s. Only one scan of the emission between 300 and 400 nm was collected per titration. The 295-nm excitation was used to select for the tryptophans in the EmrE samples. Samples were diluted and assayed in a 1-cm quartz cuvette at room temperature. A blank titration of SEC and DDM buffer alone without EmrE was performed to observe the baseline signal. All ligands were titrated to near saturation based on a ligand concentration where further titrations resulted in little to no observable change in the fluorescence intensity. Quenching of fluorescence was recorded and plotted using GraphPad PRISM 6.

Lyase Assays—

In a 2-ml polypropylene tube, microsomes containing native CYP17A1 (5 pmol) and cytochrome P450 oxidoreductase (POR) from transformed yeast were pre-incubated with heme-titrated cyt $b_5$ variants (5-20 pmol), at room temperature for 5 min before adding substrate. The reaction mixture was then diluted to 0.2 ml with 50 mM potassium phosphate buffer (pH 7.4), and substrate 17-hydroxypregnelonone (17-P5; 5 μM with 80,000 CPM in methanol, 2% of incubation volume) was added. The resulting mixture was pre-incubated at 37° C. for 3 min before adding NADPH (1 mM) and incubating at 37° C. for another 20 min. The reaction mixture was extracted with 1 ml dichloromethane, and the organic phase was dried under nitrogen flow. Steroids were analyzed using an Agilent 1260 Infinity HPLC system with UV detector and β-RAM4 in-line scintillation counter (LabLogic, Brandon, Fla.). Extracted steroid products were dissolved in 20 μl of methanol, and 5 μl injections were resolved with a 50×2.1 mm, 2.6 μm, C8 Kinetex column (Phenomenex, Torrance, Calif.), equipped with a guard column at a flow rate of 0.4 mL min$^{-1}$. A methanol/water linear gradient was used: 27% methanol from 0 to 0.5 min, 39% to 16 min, 44% to 20 min, 60% to 22 min, 71% to 30 min, 75% to 30.5 min, 27% to 33 min. Products were identified by retention times of external standards chromatographed at the beginning and ends of the experiments. The flow rate of the scintillation cocktail (Bio-SafeII, Research Products International, Mount Prospect, Ill.) was 1.2 mL min$^{-1}$, and the data were processed with Laura4 software (LabLogic).

Spectroscopic Analysis of cyt $b_5$ Redox State—

The absorbance at 409 nm ($Abs_{409}$) of the oxidized cyt $b_5$ constructs (1 nmol) in 0.2 M potassium phosphate, pH 7.5, with 0.05% CHAPS in a final volume of 0.3 mL was monitored for 2.5 min at 25° C. with data points collected every 5 sec using a Shimadzu 2600 UV-visible spectrophotometer (Addison, Ill.). For the reduction of cyt $b_5$, POR (32 pmol) was incubated with cyt $b_5$ variants (1 nmol) and 1.1 mM NADPH in 0.2 M potassium phosphate, pH 7.5, with 0.05% CHAPS in a final volume of 0.3 mL. The absorbance at 424 nm ($Abs_{424}$) was monitored as described above. Analysis included the superimposition of oxidized and reduced spectra.

Confocal Microscopy—

E. coli expressing proteins with C-terminally fused GFP were harvested and diluted 1:100 in Luria-Bertani (LB) medium. Poly-lysine (Sigma) coated slide glass was used to mount the cells. A cover glass was placed over the cells and sealed in place with clear nail polish. Cells were imaged within 1 h of their preparation with a Zeiss LSM710 confocal microscope equipped with a 100× oil immersion objective.

Dynamic Light Scattering—

Freshly purified OspA-EmrE-ApoAI* (2 µM) in 20 mM Tris 7.5, 50 mM NaCl, 5% glycerol, 1 mM EDTA pH 8.0 was equilibrated for 3 min in a sealed 15-µL quartz cuvette at 20° C. prior to recording with Dynapro Dynamics Light Scattering (Protein Solutions). A total of 30 scattering intensity acquisitions were recorded for each sample tested (10 acquisitions of 1 sec per measurement). Data were processed using Dynamics Dynapro Control Software v.6.3.40.

Negative Staining Electron Microscopy—

Freshly purified OspA-EmrE-ApoAI* was prepared at different concentrations (0.5, 0.25, 0.1 and 0.05 mg mL$^{-1}$) for negative staining by applying a 5-µL protein drop to a carbon-coated grid (300-mesh copper grid) for 2 min and blotting with filter paper to remove excess solution. A second solution of 1.5% uranyl acetate was immediately applied for another 2 min. Dried grids were examined using a FEI Tecnai 12 Spirit Twin electron microscope. Twenty fields for each sample concentration were randomly photographed at different magnification levels and later analyzed with ImageJ software.

SAXS—

Small-angle X-ray scattering (SAXS) data were collected at the Cornell High Energy Synchrotron Source (CHESS) G1 station in Ithaca, N.Y. Protein samples of ΔspMBP-EmrE-ApoAI* were exposed with a 250 µm×250 µm beam of 9.968 keV X-ray. Sample preparation included centrifugation at 30,000×g for 30 min and filtration to remove any aggregates. Samples (30 µl) were loaded and oscillated in the beam using an automated system with a plastic chip-based sample cell (2-mm path) and polystyrene X-ray transparent windows. The sample cell and X-ray flight path were placed under vacuum to reduce background scattering. Scattering patterns were captured on a Pilatus 100K-S detector (Dectris, Baden, Switzerland) at 1504-mm distance. The exposure time was 5 sec for each image and 10 images were recorded for each sample. All mathematical manipulations of the data (azimuthal integration, normalization, averaging and buffer subtraction) as well as error propagation were carried out using RAW software (Nielsen, S. S. PhD thesis, Technical University of Denmark, Kongens Lyngby, Denmark (2009), which is hereby incorporated by reference in its entirety). The range of momentum transfer was calculated to be $0.0068 < q = 4\pi \sin(\theta)/\lambda < 0.28$ Å-1, where $2\theta$ is the scattering angle and $\lambda$=1.257 Å is the X-ray wavelength. Dimer and tetramer samples were run at a range of concentrations (0.3, 0.6, 1.0, 2.0, 5.0, and 10 mg mL-1) to evaluate for possible concentration effects. Molecular weight estimated from a lysozyme standard (3.5 mg mL-1, 50 mM NaOAc, 50 mM NaCl pH 4.0) agreed with expectations within error. Radius of gyration (Rg) was calculated using both Guinier approximation (Guinier, A., "30 Years of Small-Angle X-Ray Scattering," Phys. Today 22:25 (1969), which is hereby incorporated by reference in its entirety) and the inverse Fourier transform (IFT) method as implemented in the GNOM-ATSAS 2.3 package by D. Svergun EMBL-Hamburg. The pair distance distribution function P(r) was calculated using the GNOM program (Svergun, D. I., "Determination of the Regularization Parameter in Indirect-Transform Methods Using Perceptual Criteria," J. Appl. Cryst. 25; 495-503 (1992), which is hereby incorporated by reference in its entirety). The maximum dimension of the particle, Dmax, was estimated based on the goodness of the data fit and smoothness of the decaying tail. The GNOM output file for the dimer was used as input to DAMMIF to perform ab initio shape reconstruction without imposing any symmetry. The twenty reconstructed bead models were superimposed and averaged using DAMAVER in the automatic mode. The mean normalized spatial discrepancy (NSD) was 0.636±0.047 (n=20), where an NSD value <1 indicates close agreement between different reconstructed models.

Ensemble Optimization Method (EOM) and Structural Model Refinement—

Ensemble optimization method (EOM) (Bernado et al., "Structural Characterization of Flexible Proteins Using Small-Angle X-Ray Scattering," J. Am. Chem. Soc. 129: 5656-5664 (2007), which is hereby incorporated by reference in its entirety) was used to model the flexible linkers between the three protein domains and construct possible ΔspMBP-EmrE-ApoAI* dimer models from 5 components: 1 EmrE dimer (Cryo-EM model, pdb ID: 2168), 2 ApoAI monomers (full-length ApoAI, pdb ID: 2A01 or lipid bound ApoAI, pdb ID 3K2S or ApoAI*, pdb ID 1AV1) and 2 MBP monomers (pdb ID: 1NL5). During test runs, it was found that dimer models containing the extended conformation of ApoAI (pdb ID: 3K2S and 1AV1) fit the experimental data poorly due to the large disagreement between the size of the models (average Rg=75 Å) and the measured Rg (49.85±0.99 Å, where n=4 and error is defined as standard deviation). Thus, only the compact ApoAI conformation (pdb ID: 2A01) was used for further EOM analysis. For each EOM run, 10,000 structural models are first generated. EOM then uses a genetic algorithm to select from this pool of models, an ensemble of dimer conformations, whose combined theoretical scattering intensity best describes the experimental SAXS data of the dimer. A q range of 0.009-0.28 Å-1 was used for EOM fitting. An optimized ensemble was first generated from a pool composed of half symmetric and half asymmetric models (for symmetric models, P2 symmetry was imposed), and was found to be populated with mostly symmetric models. It was also found that the overall EOM fitting assessed by ($\chi$2) values was improved when rotational freedom was allowed for the flexible GGA linker between the main bundle and the C-terminal domain of ApoAI* (FIGS. 13A-13D), indicative of the conformational change of ApoAI* upon EmrE binding. Hence, the sampling pool was refined to contain only symmetric models with free GGA linkers in ApoAI*, and a new process of ensemble optimization was conducted. The final optimized ensemble contains only 2 most populated conformations with similar configuration of the 5 components, consistent with the monodispersity observed in SAXS reconstruction of the dimer. Due to high computational cost, EOM analysis was used mainly to model inter-domain interactions. To further refine the in solution structure of the ΔspMBP-EmrE-ApoAI* dimer, especially to compare the conformational variants of the highly flexible ApoAI* protein upon binding to EmrE, several hypothetical models were built based on biochemical evidence and the structural frame provided by EOM. Agreement between the experimental data and these potential structural models was assessed by evaluating the following chi-square:

$$\overline{\chi^2} = \frac{1}{M} \sum_{i=1}^{M} \left( \frac{I_{exp}(qi) - I_{model}(qi)}{\sigma_{exp}(qi)} \right)^2 \quad \text{(Equation 1)}$$

where $I_{exp}(q_i)$ is the experimental scattering intensity at qi, Imodel (qi) is the scattering intensity calculated from models using CRYSOL[40], $\sigma_{exp}(q_i)$ is the experimental error and M is the number of data points in q space. A q range of 0.009-0.28 Å-1 was also used for the fitting. The best fit revealed by the minimal chi-square value ($\overline{\chi^2}$=0.174) is shown in FIGS. 4A-4D.

Example 2—Amphipathic ApoAI* Renders Bacterial EmrE Water Soluble

Membrane proteins are classified structurally as β-barrel or α-helical bundles. β-barrels are typically expressed as inclusion bodies, purified and refolded for structural studies whereas α-helical bundles are less likely to produce soluble active forms after refolding. To demonstrate the SIMPLEx concept, a small (110 amino acids) polytopic α-helical IMP from *E. coli* named ethidium multidrug resistance protein E (EmrE) was chosen, which is comprised of four transmembrane α-helices having 18-22 residues per helix with very short extramembrane loops. EmrE is the archetypical member of the small multidrug resistance (SMR) protein family in bacteria and confers host resistance to a wide assortment of toxic quaternary cation compounds by secondary active efflux (Bay et al., "Spectroscopic Analysis of Small Multidrug Resistance Protein EmrE in the Presence of Various Quaternary Cation Compounds," *Biochim Biophys Acta* 1818:318-1331 (2012), which is hereby incorporated by reference in its entirety).

Figure 1A:
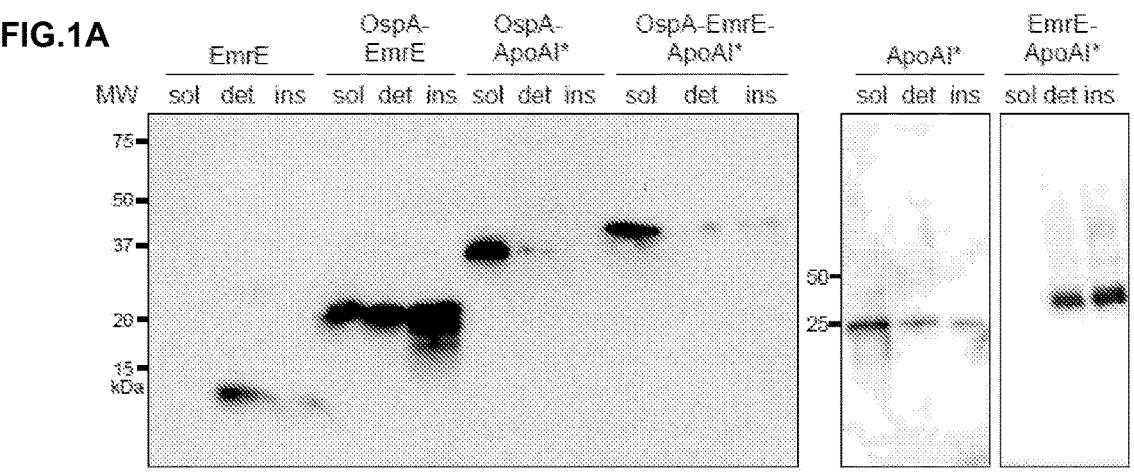
FIGS. 1A-1C show in vivo solubilization of EmrE using the SIMPLEx strategy.

To solubilize EmrE, a plasmid was created encoding a chimeric protein in which ApoAI* was fused to the C-terminus of EmrE. To prevent the secretory pathway in *E. coli* from inserting EmrE directly into the inner membrane, a highly soluble "decoy" protein from *Borrelia burgdorferi* was introduced, namely outer surface protein (OspA) (Makabe et al., "Atomic Structures of Peptide Self-Assembly Mimics," *Proc. Natl. Acad. Sci. U.S.A.* 103:17753-8 (2006), which is hereby incorporated by reference in its entirety), to the N-terminus of the EmrE-ApoAI* chimera. It was predicted that the resulting tripartite fusion would partition to the cytoplasm due to the presence of the N-terminal OspA decoy and would give rise to solubilized EmrE due to the proteic shield afforded by ApoAI*. To test this hypothesis, the cellular accumulation of OspA-EmrE-ApoAI* in *E. coli* cells transformed with pSIMPLEx-EmrE was examined. Western blot analysis of the soluble cytoplasmic fraction recovered from these cells confirmed that the tripartite fusion was a stable, water-soluble protein with hardly any of the fusion protein partitioning to the insoluble fraction (FIG. 1A). Following cell lysis and $Ni^{2+}$-affinity chromatography in the absence of detergents, approximately 10-15 mg of OspA-EmrE-ApoAI* per liter of culture was obtained. Size exclusion chromatography (SEC) confirmed that the majority of the soluble OspA-EmrE-ApoAI* were dimers and tetramers (FIG. 5A), consistent with the earlier observation that the basic functional unit of EmrE is the dimer but may also include a dimer of dimers (Elbaz et al., "In Vitro Synthesis of Fully Functional EmrE, a Multidrug Transporter, and Study of its Oligomeric State," *Proc. Natl. Acad. Sci. U.S.A.* 101:1519-24 (2004), which is hereby incorporated by reference in its entirety). Peaks corresponding to dimers and tetramers were isolated and reapplied to the SEC (FIG. 5B). Final yields of both species ranged between 8-10 mg L-1 of culture. It is worth noting that the solubility profile of OspA-EmrE-ApoAI* was nearly identical to that of a control fusion, OspA-ApoAI* lacking the IMP, which also accumulated exclusively in the soluble fraction (FIG. 1A). In stark contrast, EmrE expressed alone was detected in the detergent soluble and insoluble fractions only (FIG. 1A). A fusion comprised of OspA and EmrE without the ApoAI* domain accumulated in all three fractions of the lysate (soluble, detergent soluble, and insoluble). However, all of the soluble OspA-EmrE was aggregated as confirmed by SEC (FIG. 5C). The importance of the decoy was revealed by an EmrE-ApoAI* fusion lacking the OspA decoy, which accumulated in the detergent soluble and insoluble fractions in a manner similar to EmrE expressed alone (FIG. 1A). This insolubility was largely due to EmrE as the ApoAI* domain expressed on its own accumulated in all three fractions of the lysate (FIG. 1A).

In parallel, whether the OspA domain could be replaced with a structurally different soluble decoy, namely *E. coli* maltose-binding protein lacking its native export signal peptide (ΔspMBP), was investigated. Indeed, the tripartite ΔspMBP-EmrE-ApoAI* fusion accumulated exclusively in the soluble fraction, just like its OspA-EmrE-ApoAI* counterpart (FIG. 6A). Hence, solubilization appears to be insensitive to the identity or structure of the N-terminal domain. Moreover, when the N-terminal domain was removed by proteolytic digestion, the resulting IMP-ApoAI* cleavage product remained soluble (FIG. 6B). Together, these results suggest that the N-terminal domain functions to direct folding away from the membrane while the ApoAI* domain promotes water solubility. Since one ApoAI* monomer is capable of binding 70-100 lipids in nanodiscs (Denisov et al., "Directed Self-Assembly of Monodisperse Phospholipid Bilayer Nanodiscs with Controlled Size," *J. Am. Chem. Soc.* 126:3477-87 (2004), which is hereby incorporated by reference in its entirety), it is possible that the observed solubilization was the result of similar lipid incorporation into the fusion construct. However, when the lipid content of ΔspMBP-EmrE-ApoAI* was measured, only 5-10 lipids per monomer of ApoAI* were detected. Hence, it is concluded that the solubilization of IMPs by ApoAI* is due to protein-protein interactions and not the incorporation of a large number of lipids.

Example 3—Visualization of Solubilized EmrE in the Cytoplasm

Figure 1B:
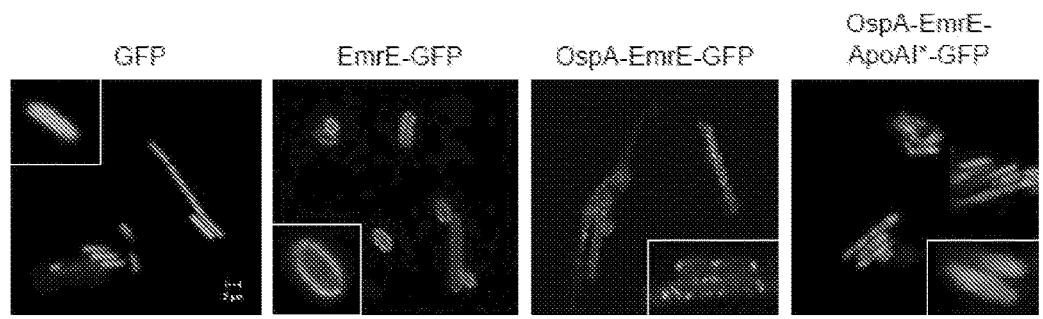
Figure 1C:
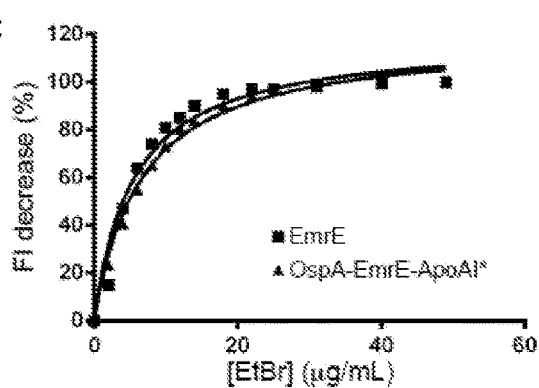

To determine the localization of the different EmrE chimeras, a green fluorescent protein (GFP) domain was added to the C-terminus of each construct. Bacterial cells synthesizing GFP-tagged membrane proteins typically exhibit a fluorescent signal that is circumferential around the cell periphery, reflecting uniform distribution of the protein within the membrane. As expected, EmrE lacking the OspA and ApoAI* domains localized in the membrane as evidenced by uniform green fluorescence appearing at the periphery of cells expressing EmrE-GFP (FIG. 1B). In contrast, diffuse cytoplasmic fluorescence was observed for cells expressing the solubilized OspA-EmrE-ApoAI*-GFP chimera (FIG. 1B), consistent with the fluorescence patterns seen for soluble GFP-tagged proteins or for GFP expressed alone. Expression of the GFP-tagged OspA-EmrE, which lacked the solubilizing ApoAI* domain, resulted in bright punctate fluorescent foci around the periphery of the cell and throughout the cytoplasm (FIG. 1B). The uneven distribution of GFP-tagged OspA-EmrE in the membrane and its accumulation at discrete locations in the cell is indicative of protein aggregation and strongly suggestive of defects in protein folding and membrane insertion, in line with the SEC results for this fusion. This would also suggest that the presence of a third protein at the C-terminus of the fusion ensemble guarantees neither the solubility nor the proper folding of the IMP. Importantly, Western blot analysis confirmed that the fluorescence observed in each of these cases was due to intact GFP fusions and not proteolytically released GFP domains (FIG. 7A).

Example 4—Solubilized EmrE Passes Folding Quality Control Checkpoint

As a final confirmation of intracellular solubility, the OspA-EmrE-ApoAI* chimera and related constructs were subjected to the folding quality control (QC) mechanism inherent to the *E. coli* twin-arginine translocation (Tat) pathway (DeLisa et al., "Folding Quality Control in the Export of Proteins by the Bacterial Twin-Arginine Translocation Pathway," *Proc. Natl. Acad. Sci. U.S.A.* 100:6115-20 (2003), which is hereby incorporated by reference in its entirety). Previous studies established that Tat QC interrogates the foldedness of its substrate proteins, allowing export of only those that are properly folded, soluble, and non-aggregated (DeLisa et al., "Folding Quality Control in the Export of Proteins by the Bacterial Twin-Arginine Translocation Pathway," *Proc. Natl. Acad. Sci. U.S.A.* 100:6115-20 (2003); Fisher et al., "Genetic Selection for Protein Solubility Enabled by the Folding Quality Control Feature of the Twin-Arginine Translocation Pathway," *Protein Sci.* 15:449-58 (2006); Rocco et al., "Twin-Arginine Translocase Mutations That Suppress Folding Quality Control and Permit Export of Misfolded Substrate Proteins," *Proc. Natl. Acad. Sci. U.S.A.* 109:13392-7 (2012), which are hereby incorporated by reference in their entirety). To determine whether any of the EmrE constructs could pass this discriminatory filter, each was modified at its N-terminus with the archetypal Tat export signal from *E. coli* trimethylamine N-oxide reductase (spTorA). This 39-residue signal peptide bears a canonical twin-arginine motif (S/T-R-R-X-F-L-K) and has been extensively used to target structurally diverse recombinant proteins for proofreading by the Tat translocase (DeLisa et al., "Folding Quality Control in the Export of Proteins by the Bacterial Twin-Arginine Translocation Pathway," *Proc. Natl. Acad. Sci. U.S.A.* 100:6115-20 (2003); Fisher et al., "Genetic Selection for Protein Solubility Enabled by the Folding Quality Control Feature of the Twin-Arginine Translocation Pathway," *Protein Sci.* 15:449-58 (2006), which are hereby incorporated by reference in their entirety). Both spTorA-OspA-EmrE-ApoAI* and spTorA-OspA-ApoAI* were capable of passing the QC filter and localizing in the periplasm (FIG. 7B), as expected for soluble, non-aggregated proteins. On the other hand, neither spTorA-EmrE nor spTorA-OspA-EmrE was exported (FIG. 7B), in agreement with their accumulation in the insoluble fraction. In the latter case, some of the spTorA-OspA-EmrE was detected in the soluble fraction, but the lack of any Tat export further suggests that the soluble OspA-EmrE is predominantly higher molecular weight aggregates that are blocked for Tat export. In all cases, detection of the cytoplasmic chaperone GroEL confirmed the integrity of fractionation (FIG. 7B). It should be pointed out that the overall expression level of spTorA-OspA-EmrE-ApoAI* detected in these experiments was visibly lower. While this could arise from poor translation and/or poor mRNA stability of the artificial fusion sequence, it is suspected that the lower expression is related to poor translocation efficiency. Even though spTorA-OspA-EmrE-ApoAI* appears to be a well-folded, soluble substrate, its export efficiency could be impeded due to its large cross-sectional area, which has been proposed as a limiting variable in the export of folded proteins by the Tat system. It is well documented that inefficiently translocated substrates are efficiently degraded as part of a poorly characterized "housecleaning" mechanism associated with that Tat system (DeLisa et al., "Folding Quality Control in the Export of Proteins by the Bacterial Twin-Arginine Translocation Pathway," *Proc. Natl. Acad. Sci. U.S.A.* 100:6115-20 (2003); Fisher et al., "Genetic Selection for Protein Solubility Enabled by the Folding Quality Control Feature of the Twin-Arginine Translocation Pathway," *Protein Sci.* 15:449-58 (2006), which are hereby incorporated by reference in their entirety), which could thus account for the lower total expression of spTorA-OspA-EmrE-ApoAI*.

Example 5—Solubilized EmrE Retains Ligand-Binding Activity

It was next determined whether EmrE that had been solubilized by fusion to ApoAI* was able to bind to known ligands. Native EmrE transports and thus binds several substrates including ethidium bromide (EtBr), methyl viologen (MV), and tetraphenylphosphonium (TPP+) (Bay et al., "Spectroscopic Analysis of Small Multidrug Resistance Protein EmrE in the Presence of Various Quaternary Cation Compounds," *Biochim Biophys Acta* 1818:1318-1331 (2012), which is hereby incorporated by reference in its entirety). There are a total of 14 aromatic amino acids in EmrE (4 tryptophans, 5 tyrosines, and 5 phenylalanines), some of which participate in ligand binding and protein stability and permit determination of binding constants based on fluorescence quenching (Bay et al., "Spectroscopic Analysis of Small Multidrug Resistance Protein EmrE in the Presence of Various Quaternary Cation Compounds," *Biochim. Biophys. Acta* 1818:1318-31 (2012), which is hereby incorporated by reference in its entirety). The ligand binding activity of dimeric, detergent-free OspA-EmrE-ApoAI* was measured and compared to detergent-solubilized EmrE. Remarkably, the binding affinity of water-soluble OspA-EmrE-ApoAI* for EtBr was very similar to that measured for detergent-solubilized EmrE, while the affinities for MV and TPP+ were each higher for ApoAI*-solubilized EmrE compared to its detergent-solubilized counterpart (FIGS. 1C and 8). Importantly, ApoAI* alone showed no measurable binding of any of the ligands. In light of these results, it should be pointed out that the environment in which ligand binding activity of EmrE is measured plays a crucial role, with binding affinity varying as a function of the membrane mimetic employed (Bay et al., "Small Multidrug Resistance Proteins: A Multidrug Transporter Family That Continues to Grow," *Biochim. Biophys. Acta* 1778: 1814-38 (2008), which is hereby incorporated by reference in its entirety). For instance, the Kd values calculated for in vitro solubilized EmrE and MV were 38.2, 5.4, and 46.2 µM when measured in small unilamellar vesicles, sodium dodecyl sulphate, or dodecylmaltoside, respectively. For in vivo solubilized EmrE, a value of 48 µM was obtained, which compares favorably with small unilamellar vesicles. On the other hand, Kd values for EtBr were similar among the three membrane mimetics and for in vivo solubilized EmrE (~5.5 04). Thus, the fact that water-soluble OspA-EmrE-ApoAI* exhibits ligand-binding activity with kinetic constants that is on par with native EmrE suggests that in vivo solubilized IMPs can be folded into a functional form.

Example 6—Solubilization of Human Cytochrome b5 by ApoAI*

Figure 2A:
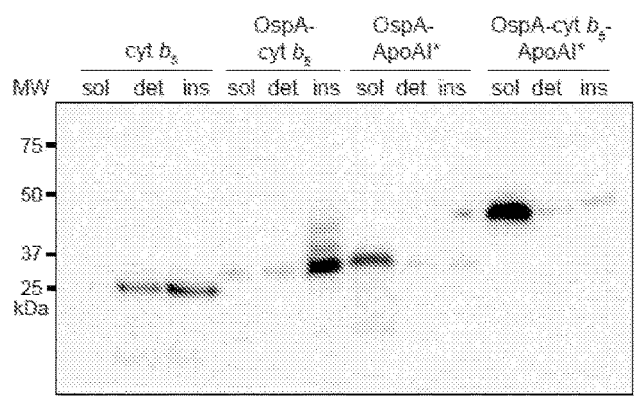
FIGS. 2A-2E show in vivo solubilization of cyt b5 using the SIMPLEx strategy.
Figure 2B:
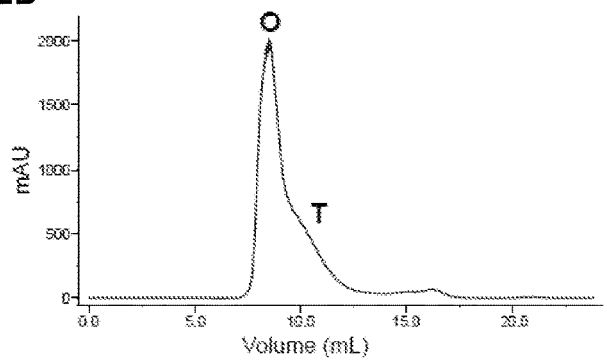
Figure 2C:
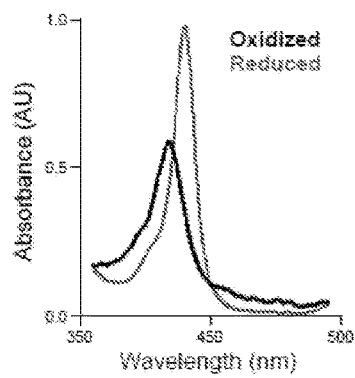
Figure 2D:
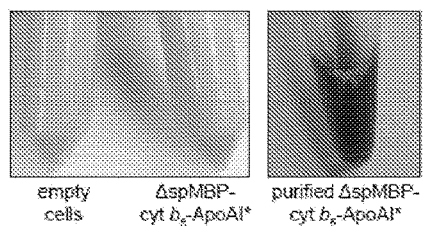
Figure 2E:
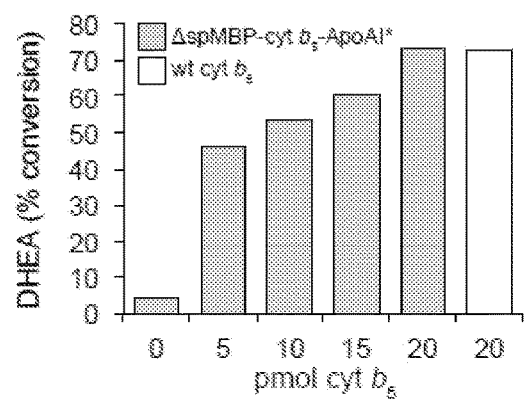
Figure 3A:
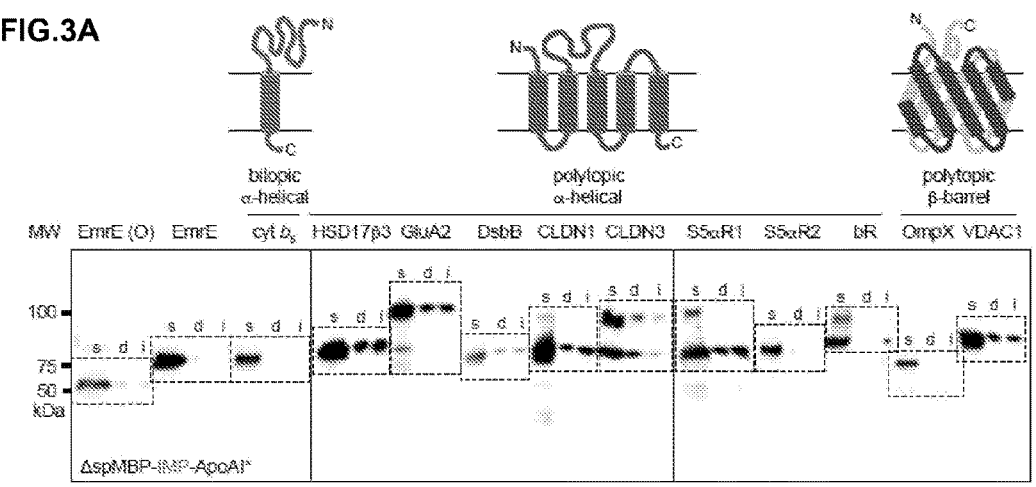
FIGS. 3A-3C show in vivo solubilization of structurally diverse IMP targets. Western blot analysis of soluble (s), detergent solubilized (d), and insoluble (i) fractions prepared from *E. coli* strain BL21(DE3) expressing.

Encouraged by the ability of ApoAI* to solubilize the polytopic bacterial EmrE, it was tested whether a structurally unrelated IMP, namely human cytochrome b5 (cyt b5), could be similarly solubilized. Cyt b5 is a 134-residue bitopic membrane protein consisting of six α-helices and five β-strands folded into three distinct domains: (i) an N-terminal heme-containing soluble domain; (ii) a C-terminal membrane anchor; and (iii) a linker or hinge region that connects the two domains. Solubility trials of OspA-cyt b5-ApoAI* resulted in an identical pattern of solubility as seen for OspA-EmrE-ApoAI* (FIG. 2A). Like EmrE, cyt b5 was similarly solubilized when the OspA decoy was replaced by ΔspMBP (FIG. 3A, lanes 7-9). The addition of ΔspMBP and ApoAI* did not affect homooligomer formation as solubilized ΔspMBP-cyt b5-ApoAI* was predominantly octameric (FIG. 2B), consistent with the oligomerization state of the detergent-solubilized enzyme (Ito et al., "Purification by Means of Detergents and Properties of Cytochrome b5 from Liver Microsomes," *J. Biol. Chem.* 243:4922-3 (1968), which is hereby incorporated by reference in its entirety). Solubilization also did not appear to disrupt heme cofactor acquisition as evidenced by the visibly red color of cells expressing ΔspMBP-cyt b5-ApoAI* and of purified ΔspMBP-cyt b5-ApoAI* (FIG. 2D), as well as by the prototypical reduced and oxidized spectra obtained for purified ΔspMBP-cyt b5-ApoAI* at 424 and 409 nm, respectively (FIG. 2C). Yields of in vivo solubilized cyt b5 were 5-8 mg L-1 of culture.

Since cofactor incorporation is obligatory for function of this IMP, it was next tested whether solubilized cyt b5 was functional. Native cyt b5 stimulates the 17,20-lyase activity of cytochrome P450c17 (17α-hydroxylase/17,20-lyase; CYP17A1). In particular, a molar equivalent of cyt b5 increases the rate of the 17,20-lyase reaction 10-fold, via an allosteric mechanism that does not require electron transfer (Auchus et al., "Cytochrome b5 Augments the 17,20-Lyase Activity of Human P450c17 Without Direct Electron Transfer," *J. Biol. Chem.* 273:3158-65 (1998), which is hereby incorporated by reference in its entirety). The ability of ΔspMBP-cyt b5-ApoAI* to stimulate lyase activity of CYP17A1 was assayed in vitro and compared to wild-type cyt b5 that had been detergent solubilized. Importantly, ΔspMBP-cyt b5-ApoAI* stimulated lyase activity in a dose-dependent manner (FIG. 2D and FIGS. 9A-9B). At these same concentrations and conditions, the stimulatory activity measured for the detergent-solubilized cyt b5 was plateaued (FIGS. 9A-9B); however, at slightly lower concentrations, detergent-solubilized cyt b5 also showed dose-dependent stimulation consistent with previous findings (Naffin-Olivos et al., "Human Cytochrome b5 Requires Residues E48 and E49 to Stimulate the 17,20-Lyase Activity of Cytochrome P450c17," *Biochemistry* 45:755-62 (2006), which is hereby incorporated by reference in its entirety). Hence, the detergent-solubilized cyt b5 was a slightly better stimulator of lyase activity than the in vivo solubilized version. Nonetheless, both enzymes were able to promote maximal stimulatory activity under the conditions tested here. Given that the C-terminal transmembrane helix of cyt b5 is required to stimulate the 17,20-lyase activity of human CYP17A1 33, it was concluded that the ApoAI* shield must be sufficiently flexible to allow protein-protein interactions that are necessary to promote proper function.

Example 7—Solubilization of Structurally Diverse IMPs Using SIMPLEx

Figure 3B:
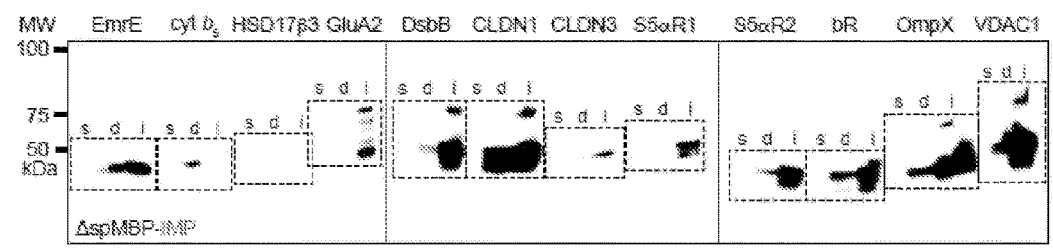
Figure 3C:
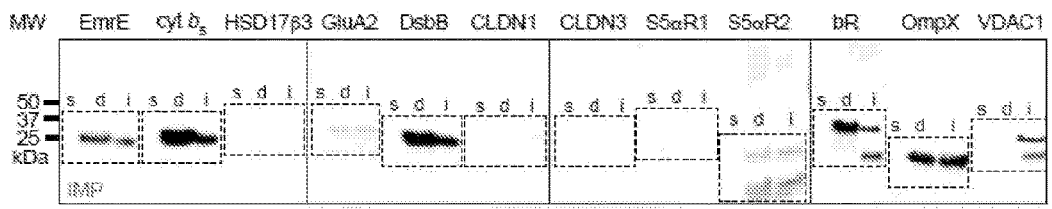

It was next sought to extend the SIMPLEx technique to a panel of ten additional IMP targets including: polytopic α-helical IMPs comprised of three (*Homo sapiens* hydroxy steroid dehydrogenase, HSD17β-3), four (*E. coli* DsbB; *H. sapiens* glutamate receptor A2, GluA2; *H. sapiens* Claudin1, CLDN1; and *H. sapiens* Claudin3, CLDN3), five (*H. sapiens* steroid 5α-reductase types 1 and 2, S5αR1 and S5αR2), or seven (*Halobacterium* sp. NRC-1 bacteriorhodopsin, bR) transmembrane helices; and polytopic β-barrel IMPs (*E. coli* OmpX and *Rattus norvegicus* voltage-dependent anion channel 1, VDAC1). Using the ΔspMBP-IMP-ApoAI* format, all ten of these IMP targets were produced at significant levels in the soluble fraction in the absence of detergents (FIGS. 3A and 10A-10B). While some of the IMP targets were also detected in the insoluble fraction, the amount of IMP partitioned in the soluble fraction was significantly higher in every case. As expected, none of the IMPs were detected in the soluble fraction when ApoAI* or both ΔspMBP and ApoAI* were omitted from the fusion (FIGS. 3B and 3C, respectively). Instead, these constructs typically partitioned to the detergent soluble and/or insoluble fractions. Moreover, for a subset of these control constructs, namely those involving HSD17β-3, GluA2, CLDN3, S5αR1 and S5αR3, little to no expression was observed in the detergent soluble fractions (FIGS. 3B and 3C). Only when these IMPs were expressed in the SIMPLEx format were they rendered soluble, suggesting that SIMPLEx is a more general strategy for creating water-soluble versions of structurally diverse IMPs.

Example 8—Structural Characterization of Solubilized EmrE

An important question is whether IMPs solubilized by the SIMPLEx strategy are amenable to structural characterization. To answer this question, attention was focused on the EmrE protein. Firstly, negative staining electron microscopy was used to observe dimeric OspA-EmrE-ApoAI* in solution. The analysis revealed a homogeneous population of monodisperse proteins (FIGS. 11A-11B). A small number of larger sized particles, deviating from the average size of approximately 5-15 nm, were observed that may represent different orientations of the soluble particles or traces of tetramers that were incompletely removed during purification.

Secondly, dynamic light scattering (DLS) was used to obtain information about the size and behavior of the fusion protein in solution. Specifically, how the solution behavior of dimeric OspA-EmrE-ApoAI* changed in the absence and presence of one of its ligand, EtBr was evaluated. Compared to the fusion protein in buffer alone, exposure to increasing amounts of EtBr resulted in a clear shift to higher molecular masses within a short period of time (~15 min, FIGS. 12A-12C). When the same fusion protein was exposed to increasing amounts of CHAPS detergent that exceeded its critical micelle concentration (cmc), the protein size did not change over time (>1 h; FIGS. 12D-12F). Taken together, these data reveal a possible conformational transition from a ligand-free dimer unit to a ligand-bound higher-degree oligomer formed by two dimers (i.e., dimer of dimers) (Elbaz et al., "In Vitro Synthesis of Fully Functional EmrE, a Multidrug Transporter, and Study of its Oligomeric State," Proc. Natl. Acad. Sci. U.S.A. 101:1519-24 (2004), which is hereby incorporated by reference in its entirety). Moreover, the ability of ApoAI* to not only solubilize EmrE but also to accommodate its native protein-protein interactions (i.e., dimer formation) all within the fusion context suggests a remarkable plasticity for this amphipathic domain.

Thirdly, biological small angle X-ray scattering (SAXS) was used to investigate the structure of EmrE in the SIM-PLEx format. This technique allows characterization of biomolecular structures in solution that can be used to formulate working models (Petoukhov et al., "Applications of Small-Angle X-ray Scattering to Biomacromolecular Solutions," Int. J. Biochem. Cell Biol. 45:429-37 (2013), which is hereby incorporated by reference in its entirety). Given the small size of OspA (~90 amino acids) and the fact that OspA-EmrE-ApoAI* appeared roughly spherical in negative staining images (FIGS. 7A-7B), it was anticipated that it might be masked in the molecular envelopes, resulting in poor data interpretation and model building. To circumvent this issue, the highly soluble and larger ΔspMBP was examined in the N-terminal position of the SIMPLEx chimera. Monodisperse ΔspMBP-EmrE-ApoAI* fusions were prepared as dimers or tetramers using $Ni^{2+}$-affinity chromatography and SEC in the absence of detergents (FIG. 6C). SAXS profiles of dimeric and tetrameric ΔspMBP-EmrE-ApoAI* were obtained at a total protein concentration of 1 mg mL-1 (FIG. 13A). The extrapolated SAXS intensity at zero angle, I(0), was proportional to molecular mass and showed the expected factor of two increase from the dimer to the tetramer samples. Differences in the size and shape of dimers and tetramers were revealed by comparing radii of gyration and pair distance distribution functions, respectively (FIG. 13B-13C). The absence of aggregation in both dimeric and tetrameric forms of ΔspMBP-EmrE-ApoAI* was confirmed by an unchanging radius of gyration as the protein concentration was increased by more than order of magnitude, to 10 mg mL-1 (FIG. 13C).

Reconstructions of the molecular envelope of dimeric ΔspMBP-EmrE-ApoAI* were computed ab initio using DAMMIF software (Franke et al., "DAMMIF, a Program for Rapid Ab-Initio Shape Determination in Small-Angle Scattering," J. Appl. Cryst. 42:342-6 (2009), which is hereby incorporated by reference in its entirety). The average of 20 bead models is shown in FIG. 4A-4D. No symmetry was imposed in the reconstruction algorithm. All 20 models are similar (mean NSD=0.636). Attempts to dock the known structures of the individual proteins into the envelope suggests an anti-parallel orientation of the two monomeric ΔspMBP-EmrE-ApoAI* units. Further evidence for this configuration of proteins in the complex arose from direct fitting of the experimental SAXS curve (I(q) vs. q) using an Ensemble Optimization Method (EOM) (Bernado et al., "Structural Characterization of Flexible Proteins Using Small-Angle X-ray Scattering," J. Am. Chem. Soc. 129: 5656-64 (2007), which is hereby incorporated by reference in its entirety). Ten thousand potential models of the ΔspMBP-EmrE-ApoAI* dimers were built from known rigid crystal structures of the three protein domains and randomly generated flexible domain linkers, resulting in a variety of possible orientations. In addition, as suggested by computational models (Phillips et al., "Predicting the Structure of Apolipoprotein A-I in Reconstituted High-Density Lipoprotein Disks," Biophys. J. 73:2337-46 (1997), which is hereby incorporated by reference in its entirety), flexible regions were assigned to the continuous helical domains observed in the ApoAI monomer structure (pdb ID: 2A01; FIG. 14). A genetic algorithm was used by EOM to select ensembles of conformations from the large pool, whose averaged theoretical scattering profile best fit the SAXS data (FIG. 13D). The final optimized ensemble of dimer models consisted predominantly of two conformations, which, interestingly, possessed similar quaternary configurations (FIG. 13D). The EOM models demonstrated that ΔspMBP proteins were on the opposite sides of the dimeric particle. When the two models were aligned together using SUP-COMB 38 (FIG. 13D), it was found that the two ApoAI* proteins tended to wrap around the EmrE dimer, consistent with the evidence of solubility observed in vivo and in detergent-free solutions. Finally, these selections were consistent with the structures that docked into the reconstructed envelope.

The lipid-binding domain of ApoAI (residues 44-243) consists of a series of eight 22-mer and two 11-mer amphipathic α-helices, which are interrupted by prolines or glycines (Li et al., "Structural Determination of Lipid-Bound ApoA-I Using Fluorescence Resonance Energy Transfer," J. Biol. Chem. 275:37048-54 (2000), which is hereby incorporated by reference in its entirety). To take into account both the high strand flexibility in the regions between the 10 helices as well as the hydrophobic shielding nature of ApoAI* against EmrE, several alternative models were constructed based on the structural framework provided by EOM. These models were compared to experimental data using CRYSOL to compute their SAXS profiles (Svergun et al., "CRYSOL—A Program to Evaluate X-ray Solution Scattering of Biological Macromolecules from Atomic Coordinates," J. Appl. Cryst. 28:768-73 (1995), which is hereby incorporated by reference in its entirety). The chi-square value was also computed and used to assess goodness of fit. The model with the lowest chi-square value ($\chi^2$=0.174) was docked into the reconstructed envelope (FIGS. 4A-4C). Based on these results, it is hypothesized that ApoAI* folds perpendicularly to the EmrE helices in a manner that resembles a shield (FIG. 4C). This requires long helices (beyond 22-mer) that resemble those of the lipid-free ApoAI protein structure (Ajees et al., "Crystal Structure of Human Apolipoprotein A-I: Insights into its Protective Effect Against Cardiovascular Diseases," Proc. Natl. Acad. Sci. U.S.A. 103:2126-31 (2006), which is hereby incorporated by reference in its entirety) (FIG. 14). In such a conformation, the last 2 helices of ApoAI form a small domain that is independent of the main helical bundle. The linker between these two domains is a pair of glycine residues (Gly185, Gly186) that provide extreme flexibility. Once the shield has been built, there is still significant hydrophobicity exposed to water where the dimers meet laterally. It is predicted that this small C-terminal domain shields this region, standing parallel to the EmrE helices. According to this shield model, protein-protein interactions between ApoAI* and EmrE promote solubilization of the IMP by shielding the "hydrophobic core" of the fusion protein from water without compromising the IMP's ability to form homo-oligomers or bind ligands.

Example 9—New Strategy for Solubilization of IMPs

Here, a new strategy for the solubilization of IMPs based on the affinity for hydrophobic surfaces displayed by amphipathic proteins is reported. This affinity was exploited to create specific protein-protein interactions in vivo between an amphipathic protein and a given IMP. Specifically, a truncated version of human apolipoprotein A-I, ApoAI*, fused to the C-terminus of an array of structurally diverse IMPs resulted in efficient in vivo solubilization of the IMP target without the need for detergents or lipid reconstitutions. By directing the expression of IMPs to the cytoplasm of E. coli, this compartment's ability to support recombinant product yields exceeding 50% of the total cellular protein (Baneyx et al., "Recombinant Protein Folding and Misfolding in Escherichia coli," Nat. Biotechnol. 22:1399-1408 (2004), which is hereby incorporated by reference in its entirety) while eliminating the energy intensive process of membrane integration is taken advantage of The end result is the accumulation of non-aggregated, water-soluble IMPs at high titers (~5-10 mg $L^{-1}$ of culture).

The yield of IMPs achieved with SIMPLEx compares favorably to previous efforts describing the production of various IMPs that were tested here. For example, ~1 mg $L^{-1}$ of EmrE was obtained using membrane-targeted expression in E. coli (Winstone et al., "Optimization of Expression and the Purification by Organic Extraction of the Integral Membrane Protein EmrE," Protein Expr. Purif. 26:111-21 (2002), which is hereby incorporated by reference in its entirety). To produce this much, EmrE required a complicated multi-step procedure involving chloroform/methanol solvent mixtures to extract EmrE followed by solubilization in SDS detergent. Moreover, as is typical for many membrane protein expression campaigns, more than 50 different variables related to culture conditions, solvent mixture ratios, and detergent choices had to be screened to identify the optimal production conditions. In contrast, in vivo solubilization using SIMPLEx yielded greater amounts of EmrE in a process that involved only standard expression and purification conditions. In the case of recombinant expression of cyt $b_5$ in E. coli, a number of strategies have been investigated. These include: (1) cytoplasmic expression of truncated cyt $b_5$ comprised of just the soluble, heme-containing domain; (2) periplasmic expression of the same soluble domain; and (3) membrane-targeted expression of the full-length cyt $b_5$. When the soluble cyt $b_5$ domain was expressed in the cytoplasm or periplasm, yields of ~5 mg $L^{-1}$ soluble protein were obtained (Beck von Bodman et al., "Synthesis, Bacterial Expression, and Mutagenesis of the Gene Coding for Mammalian Cytochrome b5," Proc. Natl. Acad. Sci. U.S.A. 83:9443-47 (1986); Karim et al., "Efficient Bacterial Export of a Eukaryotic Cytoplasmic Cytochrome," Biotechnology (N Y) 11:612-18 (1993), which are hereby incorporated by reference in their entirety). However, despite the generation of mature, heme-assembled cyt $b_5$ in soluble form, these truncated variants were incapable of stimulating 17,20-lyase activity (Lee-Robichaud et al., "Interaction of Human CYP17 (P-450(17Alpha), 17Alpha-Hydroxylase-17,20-lyase) with Cytochrome b5: Importance of the Orientation of the Hydrophobic Domain of Cytochrome b5," Biochem. J. 321(Pt 3):857-63 (1997), which is hereby incorporated by reference in its entirety). Alternatively, full-length cyt $b_5$ has been expressed in E. coli membranes with a similar yield of ~5 mg $L^{-1}$ of cell culture following extraction with acetonitrile and purification (Kaderbhai et al., "Expression, Isolation, and Characterization of a Signal Sequence-Appended Chimeric Precursor Protein," Protein Expr. Pur 7:237-46 (1996), which is hereby incorporated by reference in its entirety). Unlike the truncated variants, full-length, detergent-solubilized cyt $b_5$ stimulated 17,20-lyase activity (Lee-Robichaud et al., "Interaction of Human CYP17 (P-450 (17Alpha), 17Alpha-Hydroxylase-17,20-lyase) with Cytochrome b5: Importance of the Orientation of the Hydrophobic Domain of Cytochrome b5," Biochem. J. 321(Pt 3):857-63 (1997), which is hereby incorporated by reference in its entirety). By way of comparison, SIMPLEx yielded 5-8 mg $L^{-1}$ of full-length, heme-assembled cyt $b_5$ in a soluble conformation that stimulated lyase activity on par with the detergent-solubilized protein but without the need for detergents. Taken together, these comparisons highlight the ability of SIMPLEx to yield competitive quantities of different IMP targets using a facile, cost-effective procedure that has the potential to be transferred widely to other targets.

In the specific case of EmrE, the IMP was rendered highly soluble in the absence of detergents, exhibiting characteristics of globular proteins while retaining the IMP fold as judged by its near-native ligand binding dissociation constants. Moreover, the ApoAI*-solubilized EmrE was amenable to structural characterization including negative staining electron microscopy, DLS, and SAXS data collection. The SAXS analysis shed light on the structural plasticity that enables ApoAI* to form an amphipathic shield for sequestering IMPs from water and promoting their solubilization. Whether the flexibility of ApoAI* will present a challenge for crystallization trials is currently under investigation. It should be pointed out, however, that ApoAI itself has been crystallized (Ajees et al., "Crystal Structure of Human Apolipoprotein A-I: Insights into its Protective Effect Against Cardiovascular Diseases," Proc. Natl. Acad. Sci. U.S.A. 103:2126-31 (2006), which is hereby incorporated by reference in its entirety). Nonetheless, if flexibility proves to be an issue, it is possible to overcome this by further engineering the decoy protein, the linker length and composition, and the amphipathic protein (or use a completely different amphipathic protein altogether, which has successfully been done in related unpublished studies). The good news is that alternative methods for structure determination such as SAXS and 3D reconstruction with electron microscopy, which is advancing towards atomic resolution, are compatible with the present method. Overall, by providing high yields, proper folding, and preserved activity of target proteins, the present technique represents a powerful new addition to the toolkit for high-throughput and structural studies of IMPs of varying size and topology.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A nucleic acid construct comprising:
a chimeric nucleic acid molecule encoding a tripartite fusion protein, said chimeric nucleic acid molecule comprising:
   a first nucleic acid moiety encoding an amphipathic shield domain protein selected from the group consisting of apolipoprotein A (ApoA), apolipoprotein B (ApoB), apolipoprotein C (ApoC), apolipoprotein D (ApoD), apolipoprotein E (ApoE), apolipoprotein H (ApoH), and a peptide self-assembly mimic (PSAM);
   a second nucleic acid moiety encoding an integral membrane protein; and
   a third nucleic acid moiety encoding a water soluble expression decoy protein selected from the group consisting of outer surface protein (OspA) lacking its native export signal peptide and DnaB lacking its native export signal peptide, wherein said first nucleic acid moiety is coupled to said second nucleic acid moiety's 3' end and said third nucleic acid moiety is coupled to said second nucleic acid moiety's 5' end, said coupling being direct or indirect.

2. An expression vector comprising the nucleic acid construct of claim 1.

3. A host cell comprising the nucleic acid construct of claim 1.

4. The nucleic acid construct of claim 1, wherein the integral membrane protein is selected from the group consisting of bitopic α-helical integral membrane proteins, polytopic α-helical integral membrane proteins, integral membrane proteins with multiple helices, and polytopic β-barrel integral membrane proteins.

5. The nucleic acid construct of claim 1, wherein the apolipoprotein A is truncated ApoAI (ApoAI*).

6. An expression vector comprising the nucleic acid construct of claim 5.

7. A host cell comprising the nucleic acid construct of claim 5, wherein the host cell is *E. coli*.

8. The nucleic acid construct of claim 1, wherein the water soluble expression decoy protein is outer surface protein (OspA) lacking its native export signal peptide.

9. The nucleic acid construct of claim 5, wherein the amphipathic shield domain protein is truncated apolipoprotein A (ApoAI*) and the water soluble expression decoy protein is outer surface protein (OspA) lacking its native export signal peptide.

10. A method of recombinantly producing an integral membrane protein in water soluble form, said method comprising:

providing a host cell comprising:
   a nucleic acid construct comprising:
      a chimeric nucleic acid molecule encoding a tripartite fusion protein, said chimeric nucleic acid molecule comprising:
      a first nucleic acid moiety encoding an amphipathic shield domain protein selected from the group consisting of apolipoprotein A (ApoA), apolipoprotein B (ApoB), apolipoprotein C (ApoC), apolipoprotein D (ApoD), apolipoprotein E (ApoE), apolipoprotein H (ApoH), and a peptide self-assembly mimic (PSAM);
      a second nucleic acid moiety encoding an integral membrane protein; and
      a third nucleic acid moiety encoding a water soluble expression decoy protein selected from the group consisting of outer surface protein (OspA) lacking its native export signal peptide and DnaB lacking its native export signal peptide, wherein said first nucleic acid moiety is coupled to said second nucleic acid moiety's 3' end and said third nucleic acid moiety is coupled to said second nucleic acid moiety's 5' end, said coupling being direct or indirect; and,
culturing the host cell under conditions effective to express the integral membrane protein in a water soluble form within the host cell cytoplasm.

11. The method according to claim 10 further comprising:
recovering the integral membrane protein from the host cell following said culturing.

12. The method according to claim 11, wherein said recovering further comprises:
lysing the cell to form a cell lysate comprising a water soluble fraction and
subjecting the water soluble fraction of the cell lysate to chromatography to isolate the integral membrane protein.

13. The method according to claim 11, wherein the recovered integral membrane protein is conformationally correct.

14. The method according to claim 10, wherein the integral membrane protein is selected from the group consisting of bitopic α-helical integral membrane proteins, polytopic α-helical integral membrane proteins, integral membrane proteins with multiple helices, and polytopic β-barrel integral membrane proteins.

15. The method according to claim 10, wherein the integral membrane protein is selected from the group consisting of G protein-coupled receptors (GPCR) and olfactory receptors.

16. The method according to claim 10, wherein the chimeric nucleic acid molecule further comprises:

a promoter and a termination sequence, wherein said promoter and said termination sequence are operatively coupled to the chimeric nucleic acid molecule.

17. The method according to claim 10, wherein the chimeric nucleic acid molecule further comprises:

a linker nucleic acid moiety coupling said first, second, and/or third nucleic acid moieties together.

18. The method according to claim 10, wherein the apolipoprotein A is truncated ApoAI (ApoAI*).

19. The method according to claim 10, wherein the host cell is prokaryotic.

20. The method according to claim 10, wherein the host cell is *E. coli*.

21. The method according to claim 10, wherein the water soluble expression decoy protein is outer surface protein (OspA) lacking its native export signal peptide.

22. The method according to claim 18, wherein the amphipathic shield domain protein is truncated apolipoprotein A (ApoAI*) and the water soluble expression decoy protein is outer surface protein (OspA) lacking its native export signal peptide.

* * * * *

SEQUENCE LISTING

<160> NUMBER OF SEQ ID NOS: 7

<210> SEQ ID NO 1
<211> LENGTH: 4
<212> TYPE: PRT
<213> ORGANISM: Artificial
<220> FEATURE:
<223> OTHER INFORMATION: Linker

<400> SEQUENCE: 1

Gly Ser Gly Ser
1

<210> SEQ ID NO 2
<211> LENGTH: 5
<212> TYPE: PRT
<213> ORGANISM: Artificial
<220> FEATURE:
<223> OTHER INFORMATION: Linker

<400> SEQUENCE: 2

Gly Ser Gly Ser Gly
1               5

<210> SEQ ID NO 3
<211> LENGTH: 5
<212> TYPE: PRT
<213> ORGANISM: Artificial
<220> FEATURE:
<223> OTHER INFORMATION: Linker

<400> SEQUENCE: 3

Thr Ser Ala Ala Ala
1               5

<210> SEQ ID NO 4
<211> LENGTH: 6
<212> TYPE: PRT
<213> ORGANISM: Artificial
<220> FEATURE:
<223> OTHER INFORMATION: Linker

<400> SEQUENCE: 4

Ala Ala Ala Gly Gly Met
1               5

<210> SEQ ID NO 5
<211> LENGTH: 14
<212> TYPE: PRT
<213> ORGANISM: Artificial
<220> FEATURE:
<223> OTHER INFORMATION: Linker

<400> SEQUENCE: 5

Ala Ala Ala Gly Gly Met Pro Pro Ala Ala Ala Gly Gly Met
1               5                   10

<210> SEQ ID NO 6
<211> LENGTH: 6
<212> TYPE: PRT
<213> ORGANISM: Artificial
<220> FEATURE:
<223> OTHER INFORMATION: Linker

<400> SEQUENCE: 6

Ala Ala Ala Gly Gly Met
1               5

```
<210> SEQ ID NO 7
<211> LENGTH: 9
<212> TYPE: PRT
<213> ORGANISM: Artificial
<220> FEATURE:
<223> OTHER INFORMATION: Linker

<400> SEQUENCE: 7

Pro Pro Ala Ala Ala Gly Gly Met Met
1               5
```